United States Patent
Suddaby

(10) Patent No.: US 10,624,683 B2
(45) Date of Patent: Apr. 21, 2020

(54) SEGMENTED ALIGNMENT ROD ASSEMBLY

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 15/962,145

(22) Filed: Apr. 25, 2018

(65) Prior Publication Data
US 2019/0328424 A1    Oct. 31, 2019

(51) Int. Cl.
*A61B 17/70* (2006.01)
*A61B 17/68* (2006.01)
*A61B 17/88* (2006.01)

(52) U.S. Cl.
CPC .......... *A61B 17/707* (2013.01); *A61B 17/701* (2013.01); *A61B 17/7031* (2013.01); *A61B 17/7049* (2013.01)

(58) Field of Classification Search
CPC ............ A61B 17/7001; A61B 17/7086; A61B 17/7014; A61B 17/7035; A61B 17/7044; A61B 17/7053; A61B 17/707; A61B 17/70; A61B 17/704; A61B 17/7004; A61B 17/7011; A61B 17/7062
USPC ...................................... 606/62–64, 246–289
See application file for complete search history.

(56) References Cited

U.S. PATENT DOCUMENTS

| | | | |
|---|---|---|---|
| 5,290,289 A | 3/1994 | Sanders et al. | |
| 5,649,925 A | 7/1997 | Barbera Alacreu | |
| 5,879,352 A | 3/1999 | Filoso et al. | |
| 6,296,644 B1 | 10/2001 | Saurat et al. | |
| 6,607,530 B1 | 8/2003 | Carl et al. | |
| 7,410,489 B2 | 8/2008 | Dakin et al. | |
| 7,634,874 B2 | 12/2009 | Lucas | |
| 7,658,753 B2* | 2/2010 | Carl .................. | A61B 17/7053 606/257 |
| 7,766,941 B2 | 8/2010 | Paul | |
| 7,785,325 B1* | 8/2010 | Milbank ........... | A61B 17/7208 403/123 |

(Continued)

FOREIGN PATENT DOCUMENTS

| | | |
|---|---|---|
| WO | WO2007/086053 | 8/2007 |
| WO | WO2016/166663 | 10/2016 |
| WO | WO2017/201437 | 11/2017 |

OTHER PUBLICATIONS https://www.medicrea.com/usa/th-lumbar-range-usa/ib3e-tb. "IB3D-TB", last accessed Jul. 16, 2018.

(Continued)

*Primary Examiner* — Pedro Philogene
(74) *Attorney, Agent, or Firm* — Simpson & Simpson, PLLC

(57) ABSTRACT

A segmented rod assembly for aligning a spine having a plurality of vertebrae, including a rod, including a plurality of segments, the plurality of segments having at least a first segment arranged to be slidingly secured to a first vertebra of the spine, a second segment arranged to be fixedly secured to a second vertebra of the spine, and a third segment arranged between the first and second segments to be connected to a third vertebra of the spine, a tensioning member arranged within the plurality of segments, the tensioning member having a first end secured to the first segment and a second end.

22 Claims, 20 Drawing Sheets

(56) References Cited

U.S. PATENT DOCUMENTS

| | | | |
|---|---|---|---|
| 7,815,665 B2* | 10/2010 | Jahng | A61B 17/1757 606/254 |
| 8,114,133 B2* | 2/2012 | Logan | A61B 17/7008 606/258 |
| 8,133,241 B2 | 3/2012 | Boyd et al. | |
| 8,206,423 B2* | 6/2012 | Siegal | A61B 17/1757 606/279 |
| 8,353,935 B2 | 1/2013 | Krause | |
| 8,398,633 B2 | 3/2013 | Mueller | |
| 8,685,022 B2 | 4/2014 | Lorenz et al. | |
| 8,709,042 B2 | 4/2014 | Greenbalgh et al. | |
| 8,768,509 B2 | 7/2014 | Unsworth | |
| 8,845,690 B2 | 9/2014 | Capozzoli | |
| 9,050,112 B2 | 6/2015 | Greenhalgh et al. | |
| 9,113,783 B2 | 8/2015 | Suehara | |
| 9,144,506 B2 | 9/2015 | Phelps | |
| 9,221,179 B2 | 12/2015 | Hinman | |
| 9,333,009 B2* | 5/2016 | Kroll | A61B 17/7014 |
| 9,339,298 B1 | 5/2016 | Morales Chavarria | |
| 9,504,307 B1 | 11/2016 | Burnett et al. | |
| 9,592,132 B2 | 3/2017 | Hauck et al. | |
| 9,642,712 B2 | 5/2017 | Schaller et al. | |
| 9,668,641 B2 | 6/2017 | Ostrovsky et al. | |
| 9,763,678 B2 | 9/2017 | O'Neil et al. | |
| 2006/0058801 A1 | 3/2006 | Schlienger et al. | |
| 2008/0234691 A1 | 9/2008 | Schwab | |
| 2008/0294163 A1 | 11/2008 | Chou et al. | |
| 2009/0118771 A1 | 5/2009 | Gonzlez-Hernandez | |
| 2009/0216232 A1 | 8/2009 | Buford, II et al. | |
| 2009/0228007 A1 | 9/2009 | Justin et al. | |
| 2009/0228008 A1 | 9/2009 | Justin et al. | |
| 2010/0331842 A1 | 12/2010 | Milbank | |
| 2011/0144703 A1 | 6/2011 | Krause et al. | |
| 2013/0103091 A1 | 4/2013 | Acosta, Jr. et al. | |
| 2013/0325007 A1 | 12/2013 | Beyar et al. | |
| 2014/0358150 A1* | 12/2014 | Kaufman | A61B 17/025 606/90 |
| 2015/0257800 A1 | 9/2015 | Harshman et al. | |

OTHER PUBLICATIONS

Brochure. "ZIP Product Line, MIS Interspinous Fusion Systems", Surgical Technique Guide, Aurora Spine, Carlsbad, California, aurora-spine.com, 2014.

Mueller, Christian W. et al. "A Novel Shape Memory Plate Osteosynthesis for Noninvasive Modulation of Fixation Stiffness in a Rabbit Tibia Osteotomy Model", Hindawi Publishing Corporation, BioMed Research International, vol. 2015, Article ID 652940, 8 Pages, Http://dx.doi.org.

Barbosa, Lorena Monterio Cavalcanti et al. "Thermal Simulation of Electrical Heating of Shape Memory Alloys Wires Into a Polymeric Matrix With Two Different Sequences of Activation", 21st Brazilian Congress of Mechanical Engineering, Oct. 24-28, 2011, Natl, RN, Brazil.

Ali, Mohamed et al. "Selective RF wireless control of integrated bulk-micromachined shape-memory-alloy actuators and it's microfluidic application", Universiti Teknologi Malaysia Institutional Repository, Proceedings of the IEEE International Conference on Micro Electro Mechanical Systems (MEMS). IEEE, Cancun, http://eprints.utm.my/ID/eprint/29590., 2011, pp. 1269-1272.

* cited by examiner

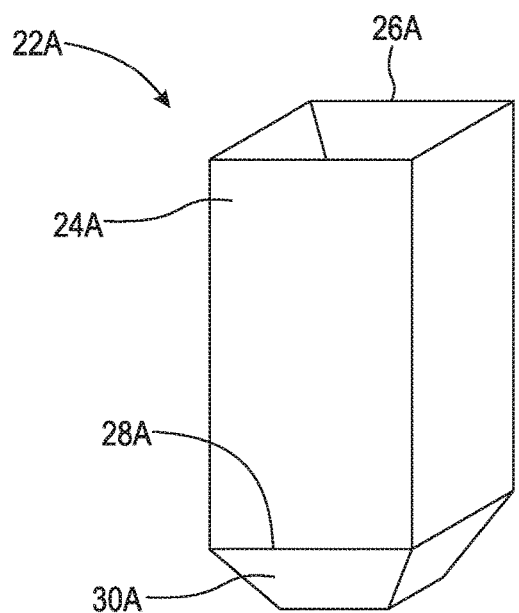
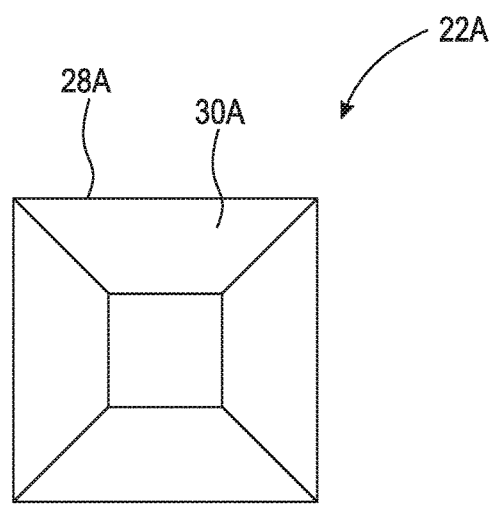
Fig. 7A
Fig. 7B
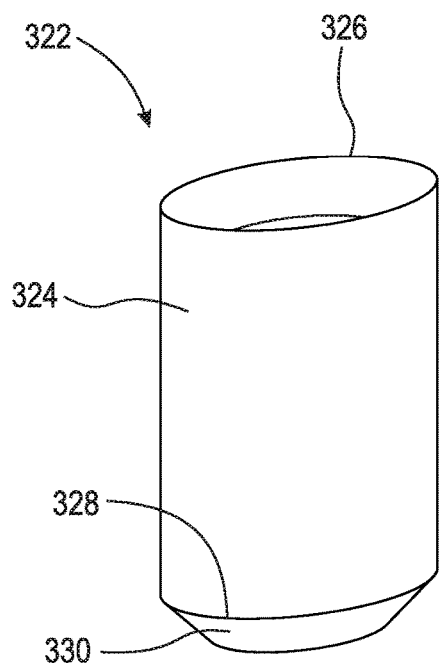
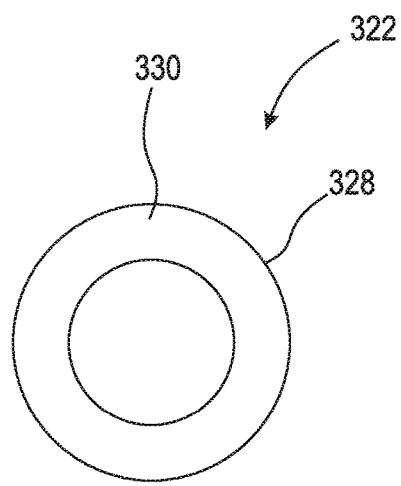
Fig. 8A
Fig. 8B

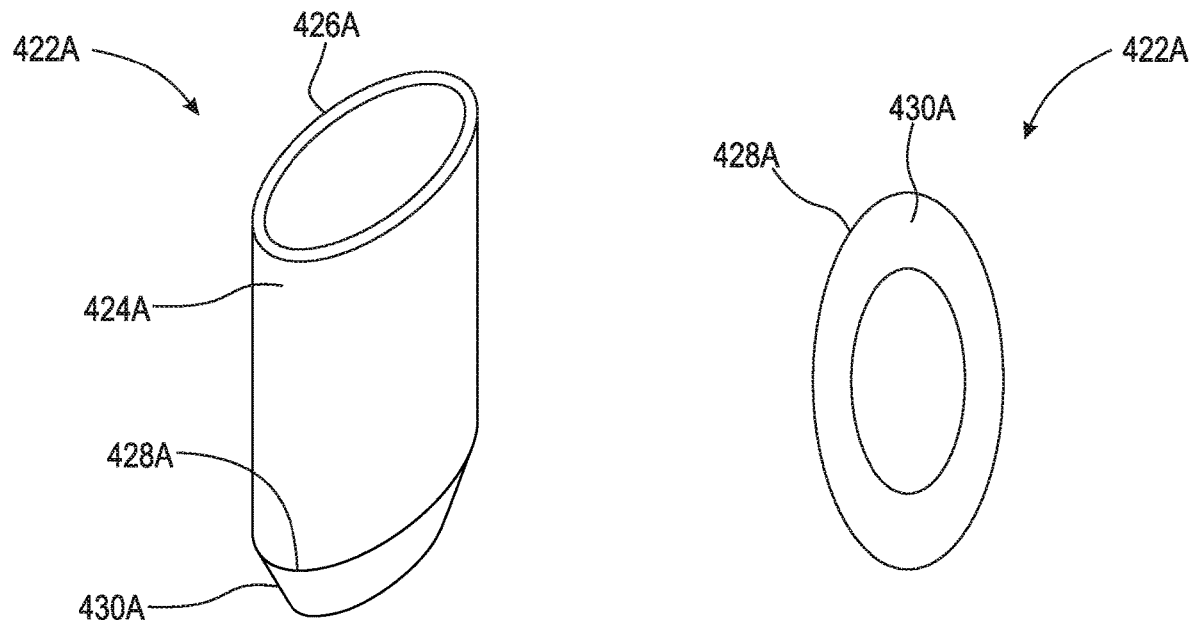
Fig. 9A
Fig. 9B
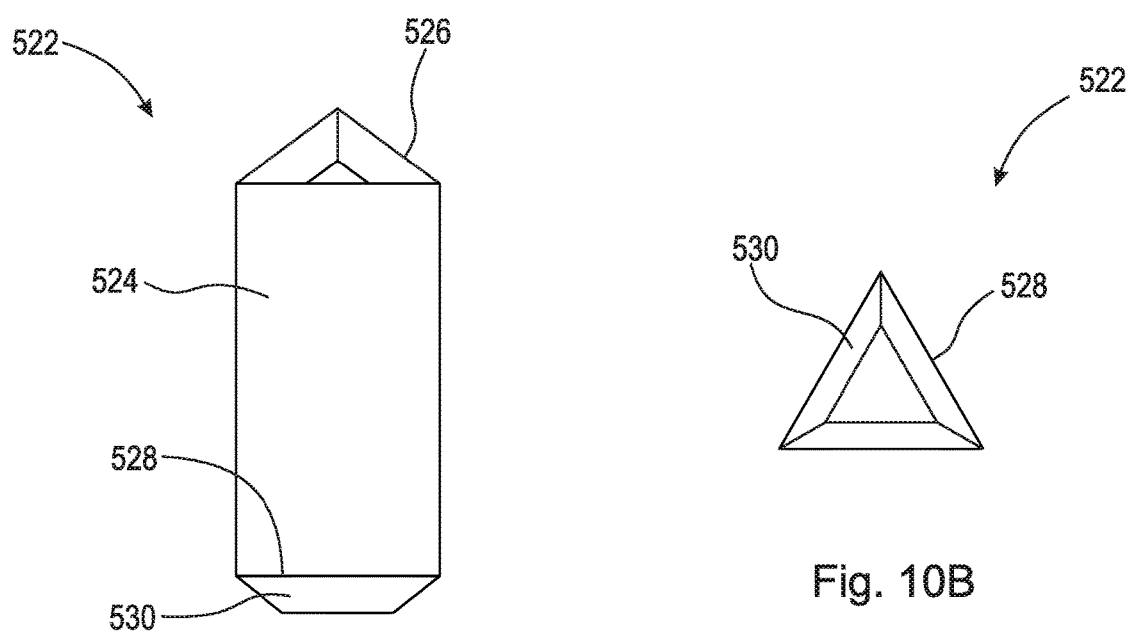
Fig. 10A
Fig. 10B

SEGMENTED ALIGNMENT ROD ASSEMBLY

FIELD

The present disclosure relates to spinal alignment, and more particularly to a segmented alignment rod assembly for performing a gradual three-dimensional alignment of a spine which has deviated from a normal attitude for pathologic reasons.

BACKGROUND

Scoliosis is a disorder that causes an abnormal curve of the spine, or backbone. Patients with scoliosis develop abnormal curves to either side of the body's median line (lateral curve) and the bones of the spine twist on each other like a corkscrew.

The Greek physician Hippocrates coined the term scoliosis and devised various forms of external braces and benches to support or stretch the abnormally curved spine. Since animals can also suffer from scoliosis, there is little doubt it is an anomaly that has been around since the dawn of vertebrates. It is estimated that about 3% of humans are afflicted, meaning over 200 million people worldwide are living with this anomaly.

Females are much more likely to suffer from scoliosis than males and for idiopathic scoliosis the ratio is 10:1. It can be seen at any age, but it is most common in those over ten years old. Present knowledge suggests a genetically predisposed growth asymmetry at the level of the vertebral body endplates as a potential underlying cause.

Minor degrees of scoliosis are treated with bracing or stretching of the spine, not that dissimilar to the prescriptions and descriptions dating back to the time of Hippocrates. While the materials and techniques have changed, the principals have evolved very little.

Severe degrees of scoliosis are largely treated by a major operation known as segmental instrumented spinal fusion, a lengthy procedure where the muscles are flayed from the spinal bone and metal rods are then implanted to straighten the spine and hold it in position until grafted bone products fuse the spinal vertebrae together into a solid tower of bone. Since the normal spine is segmented to permit functional motion, fusion in and of itself sets the stage for life long corollary problems directly related to the administered cure which precludes normal movement, and at times, even normal growth.

Because of the magnitude of the surgery, complications include death, paralysis, infection, and hardware failure. Late complications include stiffness, chronic back pain, late hardware failure, and breakdown of adjacent normal segments because of stress provided by the long fused spinal segment. This list of complications is illustrative and not exhaustive.

Since major scoliosis surgery is such a cataclysmic event, it is often employed as a last resort, meaning that simple curves are followed until major curves develop thereby increasing not only the magnitude of the surgery, but the potential risk of complications as well.

Present scoliosis treatment is rather eclectic, employing everything from techniques of bracing, essentially outlined in the time of Hippocrates, to the major robotic surgeries of present day. As with anything in medicine, whenever multiple solutions exist for a particular disease process, it generally means that no single solution is sufficiently effective.

FIG. 1 is a stylized posterior view of a person P with a spine afflicted with scoliosis. Spinal column 1 is shown to have two lateral curves—upper curve 2 and lower curve 3. Often the presence of one lateral curve generates the formation of a second curve to compensate for the reduced spinal support of the body caused by one lateral curve. FIGS. 2 and 3 depict two different types of prior art braces 4 and 5, respectively, used to prevent further deterioration of spinal alignment. In some cases, braces such as braces 4 and 5 may improve the condition, but they rarely enable the wearer to achieve a full recovery to a correct spinal alignment.

Clearly, there is a need in the art to have a treatment that is simple and safe enough to employ such that spinal curvatures can be treated early in the pathologic process so that progression to major curvature can be avoided along with the attendant major interventional surgery required when the curves are extreme.

There is also a need in the art to diminish or eradicate the requirement for fusing the spine such that normal motion can be maintained, and the deleterious consequence of a spinal fusion avoided.

SUMMARY

According to aspects illustrated herein, there is provided a segmented rod assembly for aligning a spine having a plurality of vertebrae, comprising a rod, including a plurality of segments, the plurality of segments having at least a first segment arranged to be slidingly secured to a first vertebra of the spine, a second segment arranged to be fixedly secured to a second vertebra of the spine, and a third segment arranged between the first and second segments to be connected to a third vertebra of the spine, a tensioning member arranged within the plurality of segments, the tensioning member having a first end secured to the first segment and a second end.

According to aspect illustrated herein, there is provided a segmented rod assembly for aligning a spine having a plurality of vertebrae, comprising a first clamp arranged to be secured to a first vertebra of the spine, a second clamp arranged to be secured to a second vertebra of the spine, a third clamp arranged to be secured to a third vertebra of the spine, the third vertebra located between the first vertebra and the second vertebra, a rod, including a plurality of segments, the plurality of segments having at least a first segment slidingly engaged with the first clamp a second segment fixedly secured to the second clamp, and a third segment connected to the third clamp, and a line arranged within the plurality of segments, the line having a first end secured to the first segment and a second end, and a winding mechanism arranged proximate the second segment and connected to the second end.

A segmented rod assembly for aligning a spine having a plurality of vertebrae, comprising a first clamp arranged to be secured to a first vertebra of the spine, a second clamp arranged to be secured to a second vertebra of the spine, a third clamp arranged to be secured to a third vertebra of the spine, the third vertebra located between the first vertebra and the second vertebra, a rod, including a plurality of segments, the plurality of segments having at least a first segment slidingly engaged with the first clamp, a second segment fixedly secured to the second clamp, and a third segment connected to the third clamp, and a flexible shaft arranged within the plurality of segments, the flexible shaft having a first end secured to the first segment and a second end connected to the second segment, wherein when the flexible shaft is rotated in a first circumferential direction the plurality of segments are drawn toward each other to engage.

The present disclosure broadly comprises an assembly for performing a gradual three-dimensional alignment of a spine which has deviated from a normal attitude for pathologic reasons. The assembly includes a hollow segmented rod, having segments which, when drawn together, form a contoured rod whose reconfigured shape approximates an ideal or non-pathologic spinal configuration. A cable, or cables, is housed within the hollow segments that comprise the rod. In an example embodiment, a flexible shaft assembly is housed within the hollow segments that comprise the rod. The cable, cables, and flexible shaft is designed to draw the hollow segments together such that when the segments are intimately mated, they form a rigid rod that approximates an ideal spinal alignment. The cables or flexible shaft can be drawn taut by a turnbuckle at either or both ends. The cable or turnbuckle/flexible shaft assembly, in turn, are connected to a ratcheting worm drive assembly operated by a mechanically depressible subcutaneous paddle such that gradual spinal alignment can occur as the turnbuckle shortens the intersegmental distance between rod segments and rigid rod alignment is reestablished.

The present disclosure broadly comprises an assembly for performing gradual lateral alignment of a spine, gradual sagittal alignment of a spine, or a combination of the two, as well as correcting the rotation that invariably accompanies these deviations in severe combinations of the above malalignments. In essence, correction of three dimensional malalignment.

The assembly comprises a hollow rod which is pre-contoured to approximate the normal S-shaped configuration of the human spine. The length of the rod and the approximate curves needed to correct the pathologic alignment of a patient is obtained using Surgimap® simulation software or similar software that provides computerized renderings of individual patient pathologies known in the art and presently utilized to form custom contoured patient-specific spinal rods for scoliosis surgery. Alternatively, a mathematical average for a specific spine length can be chosen and a statistical ideal curvature for the spine selected.

Once the ideal patient-specific rod is formed, it is cut into segments, with each segment being roughly the length of a vertebral body segment. In sections where little curvature is anticipated, a rod segment may span two or more vertebral segments. The preformed hollow rod is cut into segments such that each segment can deviate from the other in regard to their original axial alignment, when separated, but bond intimately in a male/female fashion when drawn together by a cable(s) or flexible shaft.

In an alternative embodiment, the adjacent segments are hinged together at a specific point at or near the circumference of the perimeter of the rod, such that the original curvilinear shape of the rod is approximated once the segments are drawn tautly together by an integrated connecting cable.

The hollow rod, once segmented, can be passed along the external surface of the spine and assume any of a myriad of pathologic configurations. The segmented rod is then affixed to the spine at the proximal and distal ends, and at the apex of the curvature, should complex rotatory curves be encountered. Individual segments are maintained in close juxtaposition by an interconnecting cable, which permits limited polyaxial movement of the segments. These segments are like beads on a string, render the construct flexible, but stiffen the construct when the string is drawn taut and the beads are pulled into close apposition. By varying the shape of the contact surfaces between the bead elements, different longitudinal shapes can be formed when the string is tautened.

The fixation of the rod to the spine will be through traditional methods known in the art such as hooks, clamps, screw, or combinations thereof. The preferred embodiment utilized a spinous process clamp which clamps two or more adjacent spinous processes. In an example embodiment, the spinous process clamp clamps only one spinous process. In the case of pedicle screws and the like, expansion screws are preferred and will be described infra.

Once the segmented rod is drawn subfacially along the pathologic spine and its curves, ideally along the spinous process/lamina junction, and affixed to the spine at two or more strategic locations, the segments are gradually drawn together to assume their original pre-segmented attitude, including the built-in contours necessary to restore perfect spinal alignment. By tensioning the cable over time, gradual spinal alignment can be achieved thereby mitigating traction injury to the spinal cord.

Drawing the segments of the rod together is accomplished in one of two ways. In highly flexible spines where forces are less likely to be extreme, the hinge and cable iteration would be chosen because it would utilize a thinner rod approximating a 5-6 mm diameter. Hinging of the segments would occur along the ventral portion of the rod where sagittal curve correction would be required and laterally where lateral curve correction is anticipated. While a round rod could be used, the hinged version may utilize an oval, or square cross-sectional shape to allow a greater surface area to employ a hinge linkage. In this version, the tautening cable would be located along the perimeter opposite the hinge, insofar as possible, to maximize the mechanical advantage. In stiffer spines, a larger 8-10 mm diameter segmented rod with a single large internal cable capable of withstanding greater force could be employed.

Once the cable rod is positioned along the spine, the hinged connection allows intimate contact of a particular rod segment with a corresponding vertebral element. The cranial and caudal segments are intimately secured via clamp, hook, or pedicle screw fixation, while the apex segment may be fixated via clamp, hook, pedicle screw, or also a cable to allow better relative movement between the alignment assembly and the spine while restoration of the spine to a normal attitude occurs. The rod segment assembly would be enclosed in a flexible sheath of biocompatible material to prevent tissue ingress or growth between rod segments, e.g., polyethylene.

Tautening of the cables occurs in the caudal segment, which houses a turnbuckle attached to the cable. A subcutaneous ratcheting worm drive mechanism is implanted in, on, or adjacent to the caudal segment and connected to a turnbuckle assembly such that when a subcutaneous paddle is digitally compressed transcutaneously through intact skin, the turnbuckle draws the cable taut thereby pulling the segments together and restoring ideal rod configuration. Since the spine is affixed to the rod, spinal movement mirrors rod movement until rigid configuration of the rod is restored. While one rod should be sufficient to restore alignment, a second rod could be employed to provide greater support of the scoliotic spine during straightening. Certain segments could connect in a ball and socket configuration to allow for limited movement of the spine thereby permitting some normal movement.

In another embodiment, a cable is replaced with a flexible rotary shaft capable of imparting both tensile and rotary forces. This shaft lies in roughly the center of the segments of the rod and is connected to a turnbuckle located at each end. Initially, the caudal turnbuckle is rotated, tensioning the system, and once it reaches maximal tensioning, it begins to rotate the flexible shaft which turns a second turnbuckle located at the cranial end. By employing two turnbuckles, even greater cable shortening and rod tensioning can occur.

To implant the segmented contoured cable rod assembly for gradual spinal alignment, the anesthetized patient is positioned prone on the operating table. After appropriate prepping and draping, fluoroscopy is used to identify the spinal curve apex as well as the cranial and caudal transition to normality. Each position is marked and a small incision is made to expose two spinous processes at each of the three indicated levels. To these exposed spinous processes, a special clamp is affixed serving to attach the segmented cable assembly to the spine. To pass the segmented cable rod assembly from one clamp to the other in subfacial location, a catheter passer is employed. Once the catheter passer is slid subfacially from one incision to another, a cable is slid through the hollow plastic sheath when the malleable trochar is removed. The wire is placed from one incision to the next entering the caudal incision, passing through the apex incision and emanating from the cranial incision. Alternatively, the cable can be passed from the cranial incision to the caudal incision, if desired. The catheter passer is removed leaving the cable behind.

Once the cable is positioned subfacially in a preferred location, the segmented cable rod assembly is attached to one end of the cable and pulled beneath the fascia along the contours of the spinal curvature. The cable rod assembly is then affixed to the spinous process clamps located at the cranial, caudal, and apex incisions.

In the preferred embodiment, the segmented cable rod assembly is securely affixed to the caudal clamp so that no relative motion, apart from segment apposition, can occur. To the caudal end of the caudal clamp, a ratcheting turnbuckle assembly is affixed and is used to draw the cable taut when a subcutaneous paddle is depressed.

In the apex incision, the segmented cable rod is affixed to the clamp such that it can slide relative to the clamp in an axial or longitudinal plane, but is restricted circumferentially by a collar. As the segmented cable rod assembly gradually straightens, it brings the spinous process clamp and spine along with it toward its new attitude. Since the rod can slide unrestricted, and has a sloppy fit, unrestricted spinal growth can occur along with some limited spinal movement. These features buffer the extremes of forces that cause failure in present day fixed scoliosis instrumented constructs, and permits a modicum of normal spinal movement for the child that rigid bracing or fusion deny.

At the superior end, the final segment of the cable rod construct affixes to the cranial clamp via a distal protuberance that engages the clamp in a piston/rod configuration. This association, similar to the collar fixation at the apex, allows for limited lateral/medial and dorsal/ventral movement while permitting linear axial movement as the child grows or whenever the child bends. The length of this slideable component is 5-7 cm to permit normal spinal growth elongation without having to lengthen the rod.

Once the assembly is affixed to the spine via the clamps the incisions are closed and allowed to heal.

Gradual spinal alignment is carried out by depressing a subcutaneous paddle beneath the skin at the level of the caudal clamp. This paddle activates a ratcheting worm drive turnbuckle assembly which tautens the cable, thereby drawing the segments of the rod closer together. As the segments approximate gradually, relative motion is restricted until a solid contoured rod assembly is formed, whereupon tightening is ceased. The rigid rod then serves to maintain normal contoured spinal alignment until mature spinal growth has been achieved. At this point, the cable is loosened and the patient is observed to ensure the mature spine does not lapse into misalignment. If it does not, the device assembly is removed, leaving a normal functioning spine. If deviation does occur, the cable assembly is retightened and fusion of the apex is carried out.

It is clear that the ratcheting worm drive mechanical activator of the present disclosure could be replaced with a magnetic, ultrasonic, or piezoelectric motor if desired. The manually operated activator is preferred in this invention so as to decrease the costs associated with this form of instrumented surgery.

Should pedicle screws be required or desired as a means of anchoring the assembly to the spine, a pedicle screw with an expansile shaft is preferred. The shaft is expanded once the screw is placed to increase surface area and mitigate "toggling" or "windshield wipering" of the shaft in softer cancellous bone when axial or perpendicular forces are applied to the shaft.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 7A is a top perspective view of a segment of the segmented rod assembly shown in FIG. 3;

FIG. 7B is a bottom elevational view of the segment shown in FIG. 7A;

FIG. 8A is a top perspective view of a segment in an example embodiment of a segmented rod assembly;

FIG. 8B is a bottom elevational view of the segment shown in FIG. 8A;

FIG. 9A is a top perspective view of a segment in an example embodiment of a segmented rod assembly;

FIG. 9B is a bottom elevational view of the segment shown in FIG. 9A;

FIG. 10A is a top perspective view of a segment in an example embodiment of a segmented rod assembly;

FIG. 10B is a bottom elevational view of the segment shown in FIG. 10A;

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be appreciated that the apex vertebra, apex, or apex of the curve is the vertebra or disk with the greatest rotation or farthest deviation from the center of the vertebral column. End vertebrae are those with the maximal tilt toward the apex of the curve.

Figure 1:
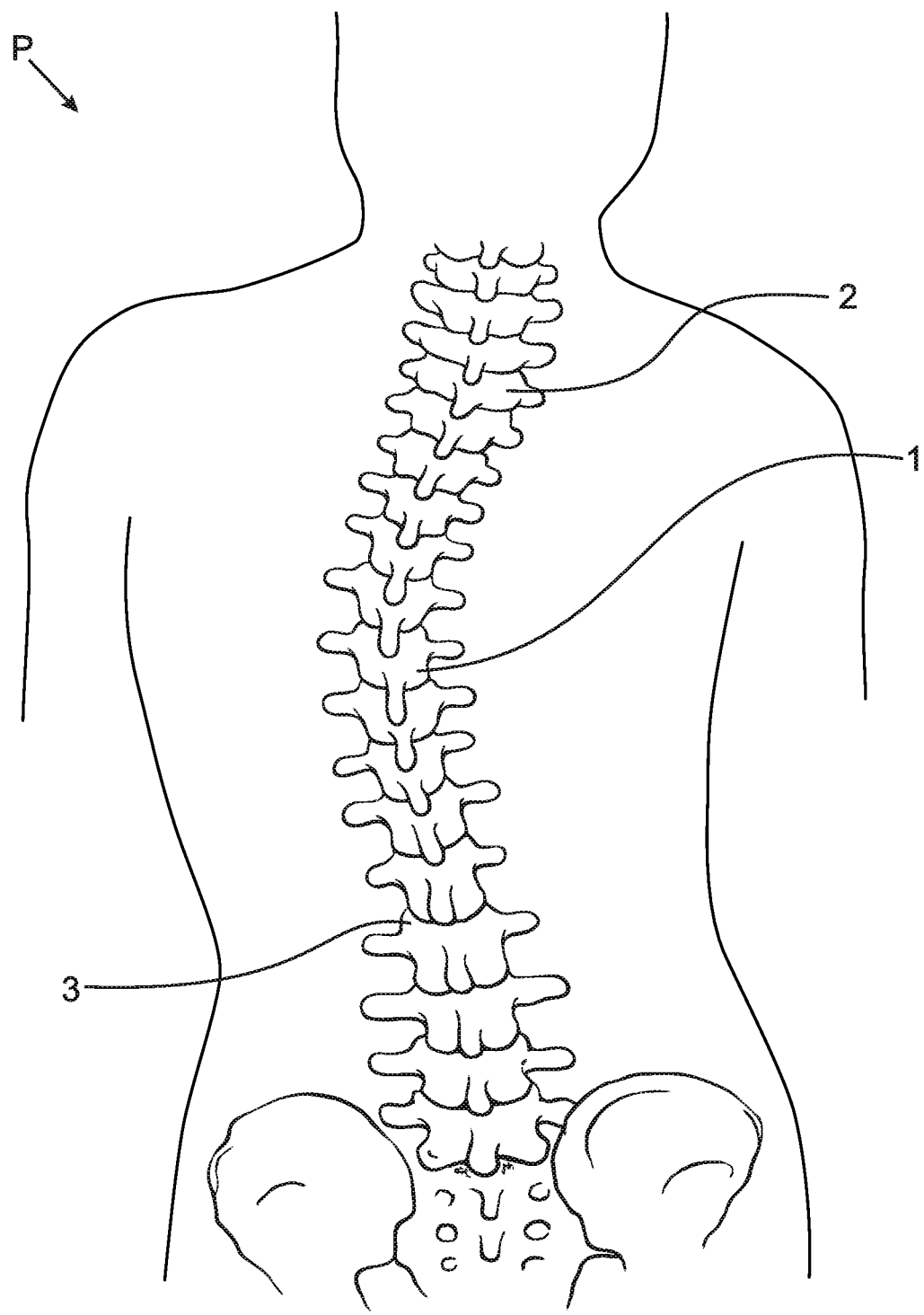
FIG. 1 is a stylized posterior view of a person with a spine afflicted with scoliosis.
Figure 3:
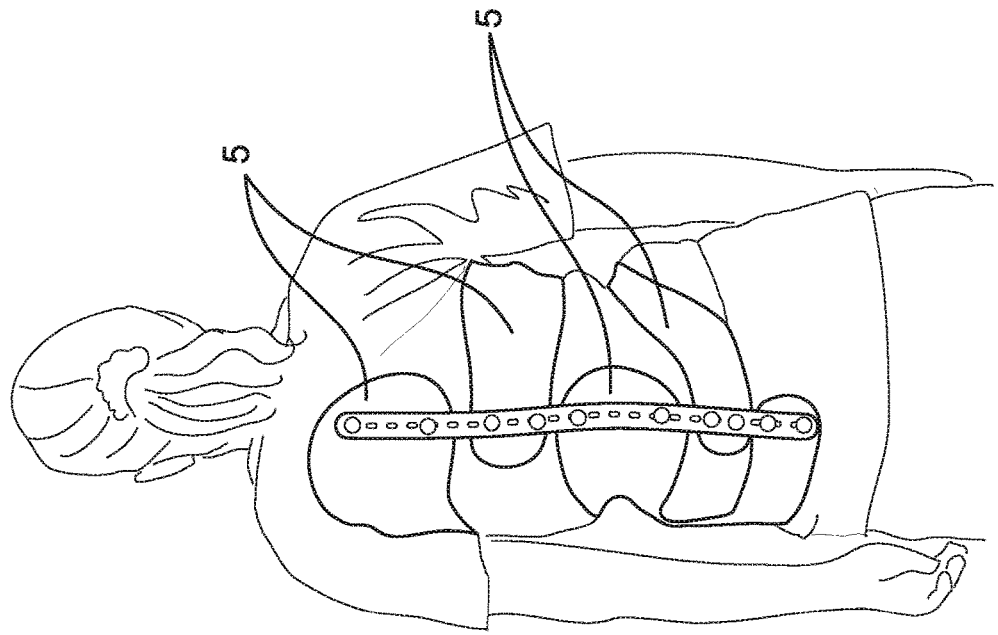
FIG. 3 is a rear view similar to that of FIG. 2 but showing a lighter prior art brace.
Figure 2:
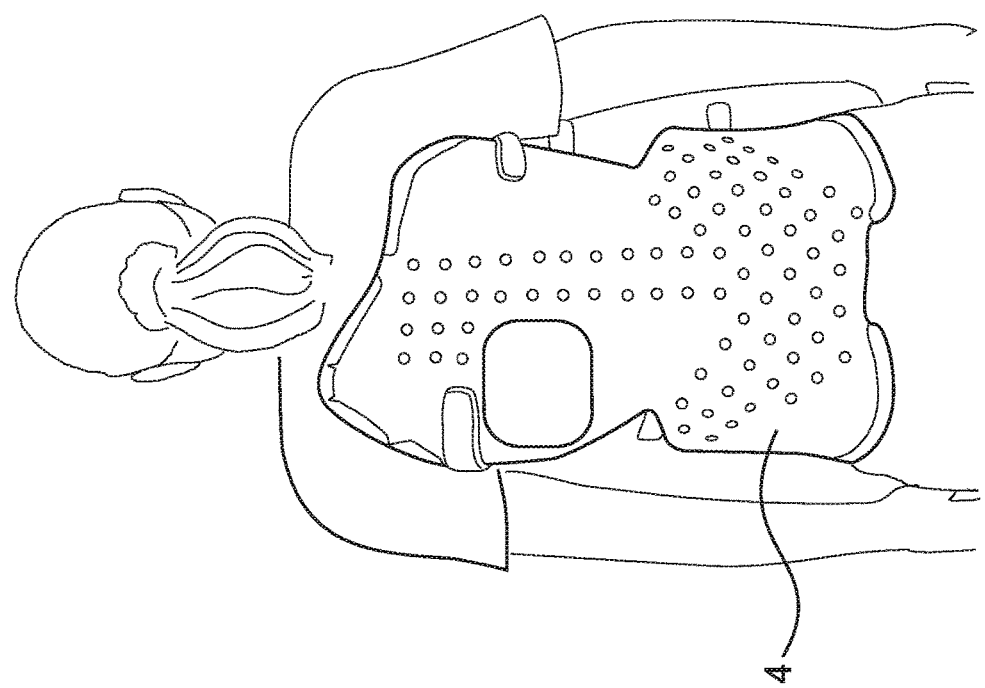
FIG. 2 is a rear view of a person with scoliosis wearing a full body brace as known in the prior art.
Figure 4A:
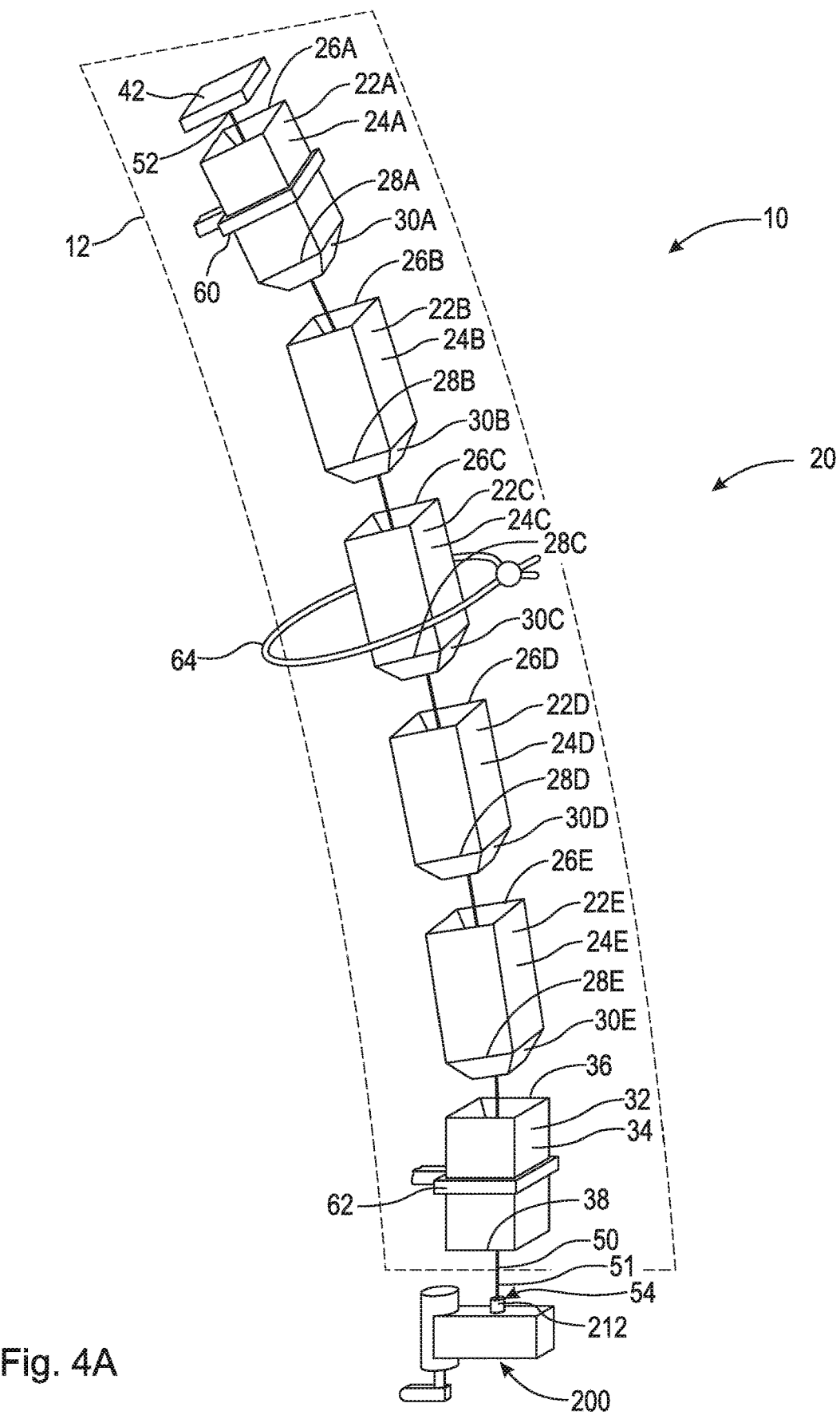
FIG. 4A is a perspective view of a segmented rod assembly.

Referring now to the figures, FIG. 4A is a perspective view of segmented rod assembly 10. Segmented rod assembly 10 comprises rod 20, tensioning member 50, and winding assembly 200. Segmented rod assembly 10 may be enclosed or at least partially enclosed in flexible sheath 12. Flexible sheath 12 comprises a biocompatible material (e.g., polyethylene) to prevent tissue ingress or growth between rod segments.

Rod 20 comprises a plurality of segments arranged adjacent each other along tensioning member 50. In the embodiment shown, rod 20 is generally a hollow rod comprising segments 22A-E and 32. Segments 22A-E are substantially similar, but may differ in length. Preferably, each of segments 22A-E comprises a length which is similar to that of the height of a vertebra. In an example embodiment, the segments proximate an extreme curvature of a pathologic spine may comprise a smaller height than the segments proximate a straighter spine curvature. This arrangement allows for a more gradual and efficient straightening of the pathologic spine. Rod 20 may comprise plastic (e.g., polyethylene), titanium, chromium, cobalt, or any other suitable material.

Segment 22A comprises body 24A, end 26A, end 28A, and engaging member 30A. Engaging member 30A is connected to end 28A and tapers therefrom. Engaging member 30A is arranged to engage end 26B of segment 22B. Segment 22B comprises body 24B, end 26B, end 28B, and engaging member 30B. Engaging member 30B is connected to end 28B and tapers therefrom. Engaging member 30B is arranged to engage end 26C of segment 22C. Segment 22C comprises body 24C, end 26C, end 28C, and engaging member 30C. Engaging member 30C is connected to end 28C and tapers therefrom. Engaging member 30C is arranged to engage end 26D of segment 22D. Segment 22D comprises body 24D, end 26D, end 28D, and engaging member 30D. Engaging member 30D is connected to end 28D and tapers therefrom. Engaging member 30D is arranged to engage end 26E of segment 22E. Segment 22E comprises body 24E, end 26E, end 28E, and engaging member 30E. Engaging member 30E is connected to end 28E and tapers therefrom. Engaging member 30E is arranged to engage end 36 of segment 32. Segment 32 comprises body 34, end 36, and end 38. End 38 is arranged to engage a tensioning or winding assembly. As shown, end 38 is arranged to abut against and/or secure to winding assembly 200. It should be appreciated that rod 20 may have any number of segments suitable to be secured to and gradually straighten a pathologic spine. As is apparent to one having ordinary skill in the art, rod 20 must have enough segments to adequately canvas the subject curvature of the pathologic spine.

Tensioning member 50 is arranged inside of rod 20. Specifically, tensioning member 50 passes through segments 22A-E and 32. In the embodiment shown, tensioning member 50 is embodied as line 51 having end 52 and end 54. Line 51 may be a cable, plurality of cables, string, rope, chain, or any other flexible material suitable to draw segments 22A-E and 32 together upon tautening. End 52 is connected to plate 42. Plate 42 is arranged to abut against or connect to end 26A. In an example embodiment, plate 42 is integrally formed with segment 22A and is fixed to end 26A. End 54 extends through segment 32 out of end 38 and is connected to a tensioning or winding assembly (e.g., winding assembly 200). The arrangement of segments 22A-E and 32 on line 51 resembles that of beads on a string. As line 51 is tautened via winding assembly 200, plate 42 pulls segments 22A-E and 32 together. As segments 22A-E and 32 begin to engage, rod 20 becomes increasingly rigid. Once segments 22A-E and 32 are fully engaged, rod 20 resembles a single rigid rod.

In an example embodiment, end 54 may be connected to a turnbuckle rod which threadably engages segment 32. Specifically, the turnbuckle rod is a threaded rod which threadably engages end 38 at a first end and has a hook at its second end which is connected to end 54 of line 51. As the turnbuckle rod is rotated, the hook pulls end 54 toward end 38 and thereby tautens line 51. In an example embodiment, end 54 may be connected to a turnbuckle rod which threadably engages segment 22A. Specifically, the turnbuckle rod is a threaded rod which threadably engages end 26A at a first end and has a hook at its second end which is connected to end 52 of line 51. As the turnbuckle rod is rotated, the hook pulls end 54 toward end 38 and thereby tautens line 51. In an example embodiment, there are turnbuckles arranged in both segment 22A and 32. Line 51 may be connected to a hook on the respective turnbuckle rod via a loop or directly connected to the respective turnbuckle via welding, adhesives, etc.

Segmented rod assembly 10 further comprises a plurality of anchors. As shown, segmented rod assembly 10 comprises anchors 60, 62, and 64 for connecting rod 20 to the pathologic spine. Anchor 60 is slidably connected to segment 22A and is secured to a cranial vertebra using, for example, a spinous process clamp, a pedicle screw, or other similar method of fixation. Anchor 60 is slidably connected to segment 22A such that as the pathologic spine straightens, and thereby lengthens, segmented rod assembly 10 adjusts to the length of the spine. To account for the increase in length, segment 22A may be significantly longer than the other segments. Anchor 62 is fixedly secured to segment 32 and is secured to a caudal vertebra using, for example, a spinous process clamp, a pedicle screw, or other similar method of fixation. Anchor 64 is slidably connected to segment 22C and is connected to the apex vertebra. Similar to anchor 60, anchor 64 is slidably connected to segment 22C to adjust for the straightening and lengthening of the spine. In an example embodiment, anchor 64 is fixedly connected to segment 22C. It should be appreciated that anchor 64 does not need to be slidably connected to segment 22C, but can be connected to any segment that is arranged near the apex vertebra such that the pathologic spine may be suitably straightened.

Figure 4B:
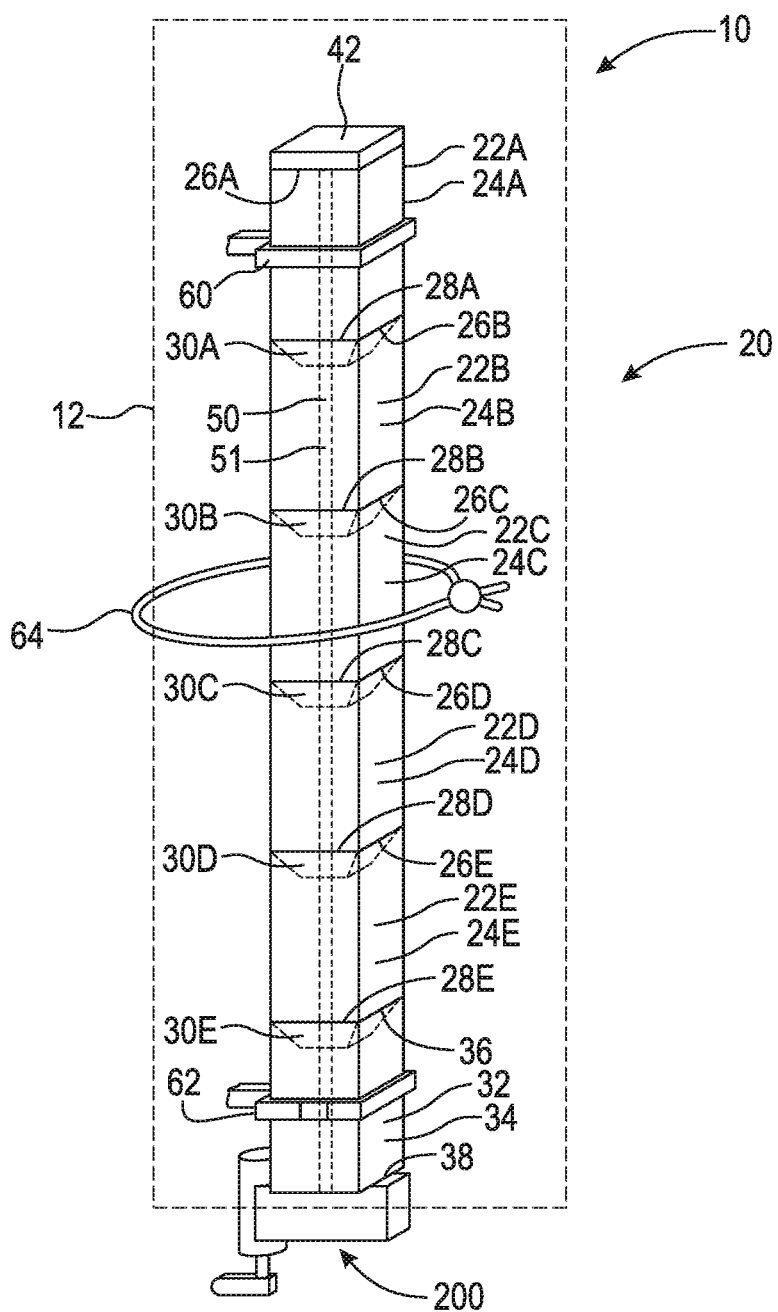
FIG. 4B is a perspective view of the segmented rod assembly shown in FIG. 4A, in a rigid rod alignment.

FIG. 4B is a perspective view of segmented rod assembly 10 in a rigid rod alignment. As shown, the segments of rod 20 are fully engaged with each other. Line 51 is tautened by winding assembly 200 such that plate 42 is pulled toward winding assembly 200. Plate 42 abuts against end 26A of segment 22A. Engaging member 30A is fully engaged with segment 22B such that end 28A abuts against end 26B. Engaging member 30B is fully engaged with segment 22C such that end 28B abuts against end 26C. Engaging member 30C is fully engaged with segment 22D such that end 28C abuts against end 26D. Engaging member 30D is fully engaged with segment 22E such that end 28D abuts against end 26E. Engaging member 30E is fully engaged with segment 32 such that end 28E abuts against end 36. Additionally, end 38 abuts against winding assembly 200. As previously mentioned, in an example embodiment winding assembly 200 is fixedly secured to end 38 of segment 32 and/or plate 42 is fixedly secured to end 26A of segment 22A.

It should be appreciated that rod 20, when rigid, does not need to form a linear rod. The design of rod 20, when rigid, imitates the normal curvature of the human spine (i.e., thoracic curvature, sacral curvature, lumbar curvature, cervical curvature, lateral curvature, etc.). FIG. 4B demonstrates simply how the various segments engage in order form a rigid rod. The rod shown in FIG. 4B could be employed to correct lateral curvature of a pathologic spine.

Figure 5A:
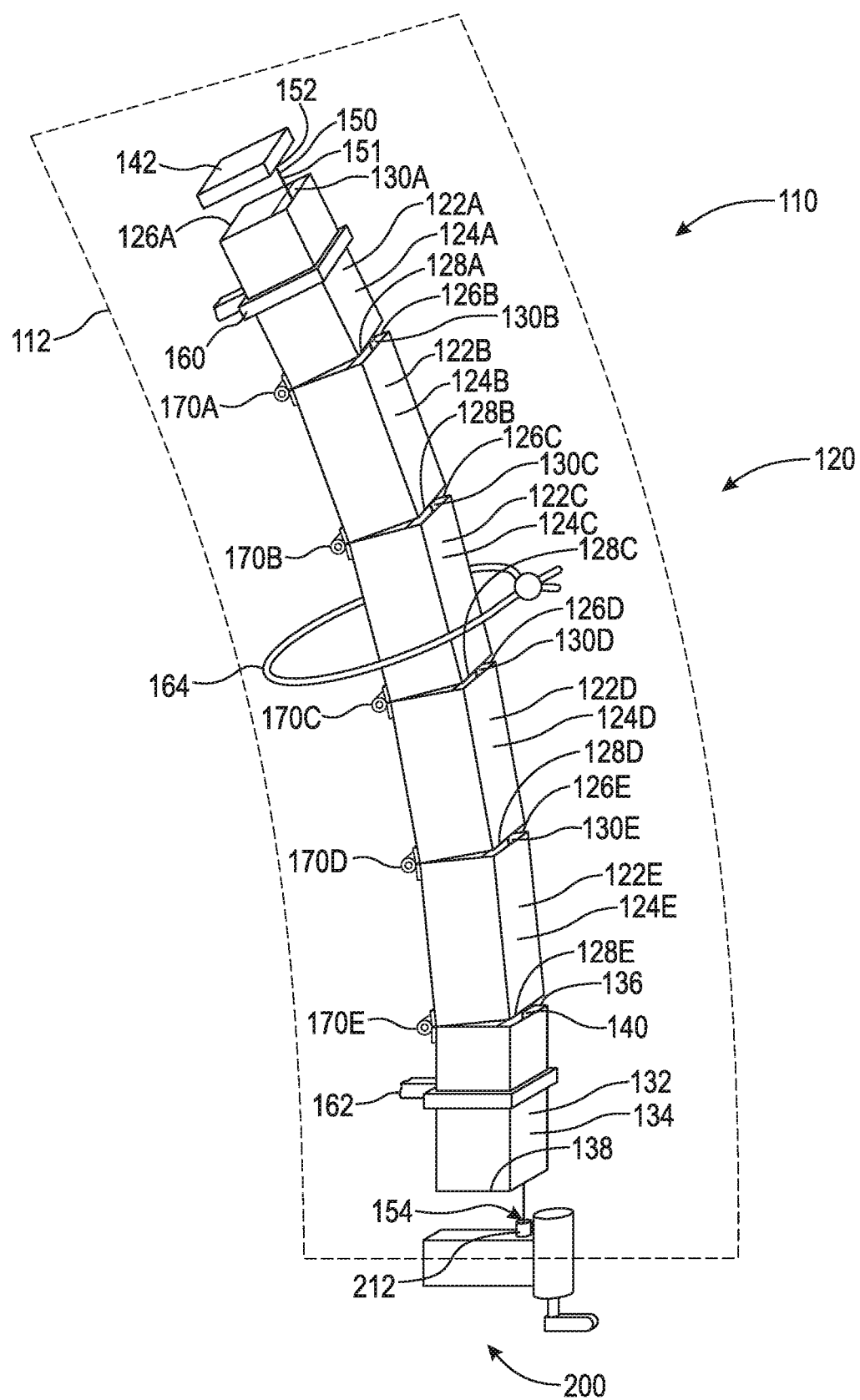
FIG. 5A is a perspective view of a segmented rod assembly.

FIG. 5A is a perspective view of segmented rod assembly 110. Segmented rod assembly 110 comprises rod 120, tensioning member 150, and winding assembly 200. Segmented rod assembly 110 may be enclosed or at least partially enclosed in flexible sheath 112. Flexible sheath 112 comprises a biocompatible material (e.g., polyethylene) to prevent tissue ingress or growth between rod segments.

Rod 120 comprises a plurality of segments arranged adjacent each other along tensioning member 150. In the embodiment shown, rod 120 is generally a hollow rod comprising segments 122A-E and 132. Segments 122A-E are substantially similar, but may differ in length. Preferably, each of segments 122A-E comprises a length which is similar to that of the height of a vertebra. In an example embodiment, the segments proximate an extreme curvature of a pathologic spine may comprise a smaller height than the segments proximate a straighter spine curvature. This arrangement allows for a more gradual and efficient straightening of the pathologic spine. Rod 120 may comprise plastic (e.g., polyethylene), titanium, chromium, cobalt, or any other suitable material.

Segment 122A comprises body 124A, end 126A, and end 128A. Segment 122B comprises body 124B, end 126B, and end 128B. Segment 122C comprises body 124C, end 126C, and end 128C. Segment 122D comprises body 124D, end 126D, and end 128D. Segment 122E comprises body 124E, end 126E, and end 128E. Segment 132 comprises body 134, end 136, and end 138. End 138 is arranged to engage a tensioning or winding assembly. As shown, end 138 is arranged to abut against and/or secure to winding assembly 200. It should be appreciated that rod 120 may have any number of segments suitable to be secured to and gradually straighten a pathologic spine. As is apparent to one having ordinary skill in the art, rod 120 must have enough segments to adequately canvas the subject curvature of the pathologic spine.

Segment 122B is hingedly connected to segment 122A, for example, via hinge 170A. Hinge 170A is arranged between segments 122A and 122B such that, when rigid, end 128A abuts against end 126B. Segment 122C is hingedly connected to segment 122B, for example, via hinge 170B. Hinge 170B is arranged between segments 122B and 122C such that, when rigid, end 128B abuts against end 126C. Segment 122D is hingedly connected to segment 122C, for example, via hinge 170C. Hinge 170C is arranged between segments 122C and 122D such that, when rigid, end 128C abuts against end 126D. Segment 122E is hingedly connected to segment 122D, for example, via hinge 170D. Hinge 170D is arranged between segments 122D and 122E such that, when rigid, end 128D abuts against end 126E.

Segment 132 is hingedly connected to segment 122E, for example, via hinge 170E. Hinge 170E is arranged between segments 122E and 132 such that, when rigid, end 128E abuts against end 136. It should be appreciated that the hinges may be arranged on any side of the segments to accommodate for three-dimensional alignment (e.g., if a pathologic spine has problematic curvature in both the coronal and the sagittal directions).

Tensioning member 150 is arranged inside of rod 120. Specifically, tensioning member 150 passes through segments 122A-E and 132. In the embodiment shown, tensioning member 150 is embodied as line 151 having end 152 and end 154. End 152 is connected to plate 142. Plate 142 is arranged to abut against or connect to end 126A. In an example embodiment, plate 142 is integrally formed with segment 122A and is fixed to end 126A. End 154 extends through segment 132 out of end 138 and is connected to a tensioning or winding assembly (e.g., winding assembly 200). The arrangement of segments 122A-E and 132 on line 151 resembles that of beads on a string. As line 151 is tautened via winding assembly 200, plate 142 pulls segments 122A-E and 32 together, thereby "closing the hinges." As segments 122A-E and 132 begin to engage, rod 120 becomes increasingly rigid. Once segments 122A-E and 132 are fully engaged, rod 120 resembles a single rigid rod.

In an example embodiment, end 154 may be connected to a turnbuckle rod which threadably engages segment 132. Specifically, the turnbuckle rod is a threaded rod which threadably engages end 138 at a first end and has a hook at its second end which is connected to end 154 of line 151. As the turnbuckle rod is rotated, the hook pulls end 154 toward end 138 and thereby tautens line 151. In an example embodiment, end 154 may be connected to a turnbuckle rod which threadably engages segment 122A. Specifically, the turnbuckle rod is a threaded rod which threadably engages end 126A at a first end and has a hook at its second end which is connected to end 152 of line 151. As the turnbuckle rod is rotated, the hook pulls end 154 toward end 138 and thereby tautens line 151. In an example embodiment, there are turnbuckles arranged in both segment 122A and 132. Line 151 may be connected to a hook on the respective turnbuckle rod via a loop or directly connected to the respective turnbuckle via welding, adhesives, etc.

In an example embodiment, and as shown in FIG. 5, segmented rod assembly 110 may comprise partitions in each segment. Preferably, line 151 is arranged along the side of the segment opposite the hinge to allow for complete abutment between segments. As such, segment 122A comprises partition 130A, segment 122B comprises partition 130B, segment 122C comprises partition 130C, segment 122D comprises partition 130D, segment 122E comprises partition 130E, and segment 132 comprises partition 140. Line 151 passes through the segments and is arranged in each respective partition. In an example embodiment, segments 122A-E and 132 may be solid with partitions being through-bores extending axially there through.

Segmented rod assembly 110 further comprises a plurality of anchors. As shown, segmented rod assembly 110 comprises anchors 160, 162, and 164 for connecting rod 120 to the pathologic spine. Anchor 160 is slidably connected to segment 122A and is secured to a cranial vertebra using, for example, a spinous process clamp, a pedicle screw, or other similar method of fixation. Anchor 160 is slidably connected to segment 122A such that as the pathologic spine straightens, and thereby lengthens, segmented rod assembly 110 adjusts to the length of the spine. To account for the increase in length, segment 122A may be significantly longer than the other segments. Anchor 162 is fixedly secured to segment 132 and is secured to a caudal vertebra using, for example, a spinous process clamp, a pedicle screw, or other similar method of fixation. Anchor 164 is slidably connected to segment 122C and is connected to the apex vertebra. Similar to anchor 160, anchor 164 is slidably connected to segment 122C to adjust for the straightening and lengthening of the spine. In an example embodiment, anchor 164 is fixedly connected to segment 122C. It should be appreciated that anchor 164 does not need to be slidably connected to segment 122C, but can be connected to any segment that is arranged near the apex vertebra such that the pathologic spine may be suitably straightened.

Figure 5B:
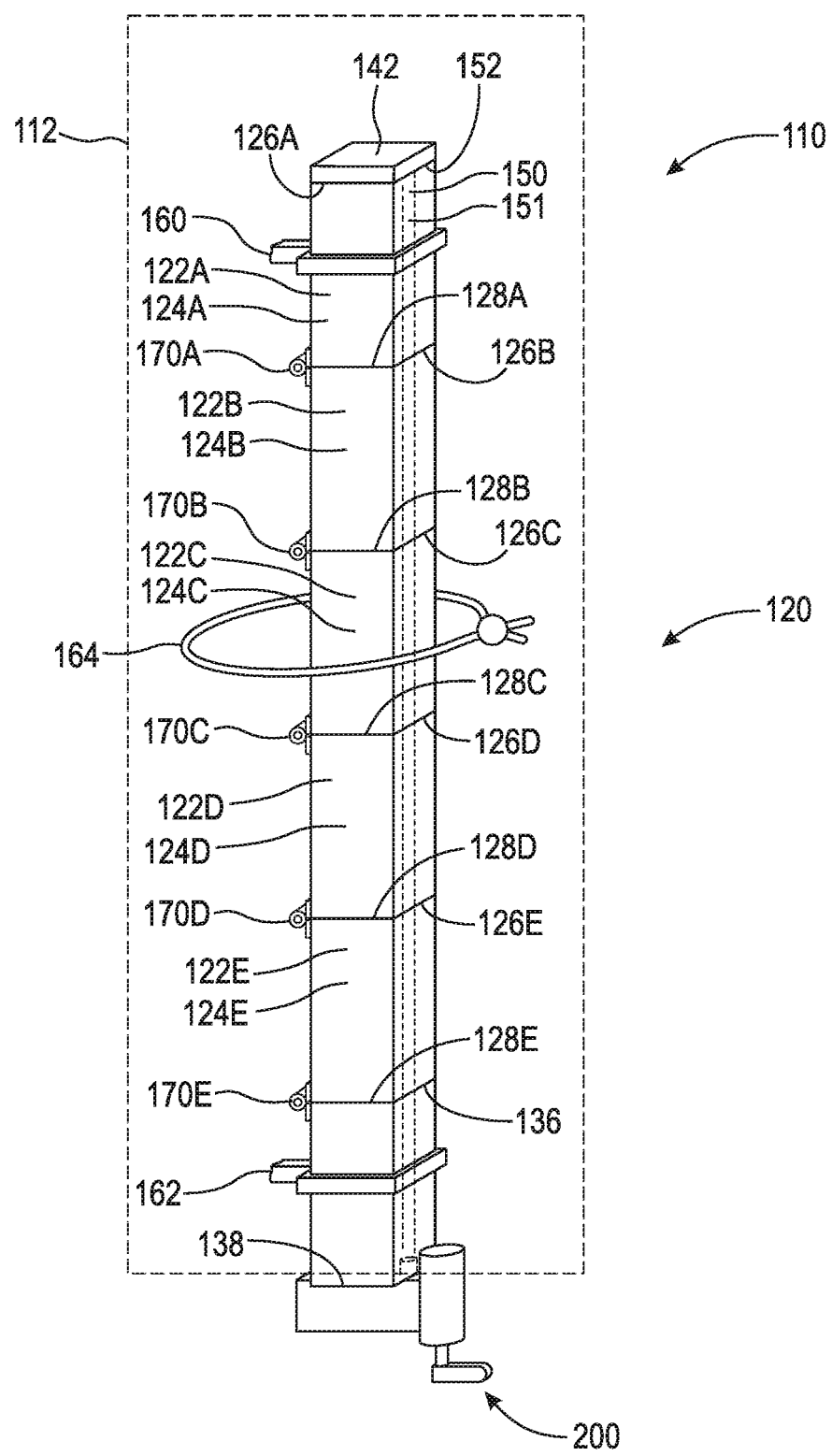
FIG. 5B is a perspective view of the segmented rod assembly shown in FIG. 5A, in a rigid rod alignment.

FIG. 5B is a perspective view of segmented rod assembly 110 in a rigid rod alignment. As shown, the segments of rod 120 are fully engaged with each other (i.e., the segments are completely abutted against each other). Line 151 is tautened by winding assembly 200 such that plate 142 is pulled toward winding assembly 200. Plate 142 abuts against end 126A of segment 122A. When rod 120 is fully rigid, end 128A abuts against end 126B, end 128B abuts against end 126C, end 128C abuts against end 126D, end 128D abuts against end 126E, and end 128E abuts against end 136. Additionally, end 138 abuts against winding assembly 200. As previously mentioned, in an example embodiment winding assembly 200 is fixedly secured to end 138 of segment 132 and/or plate 142 is fixedly secured to end 126A of segment 122A.

It should be appreciated that rod 120, when rigid, does not need to form a linear rod. The design of rod 120, when rigid, may imitate the normal curvature of the human spine (i.e., thoracic curvature, sacral curvature, lumbar curvature, cervical curvature, etc.). FIG. 5B demonstrates simply how the various segments engage in order form a rigid rod. The rod shown in FIG. 5B could be employed to correct lateral curvature or abnormal sagittal or rotational curvature of a pathologic spine.

Figure 6A:
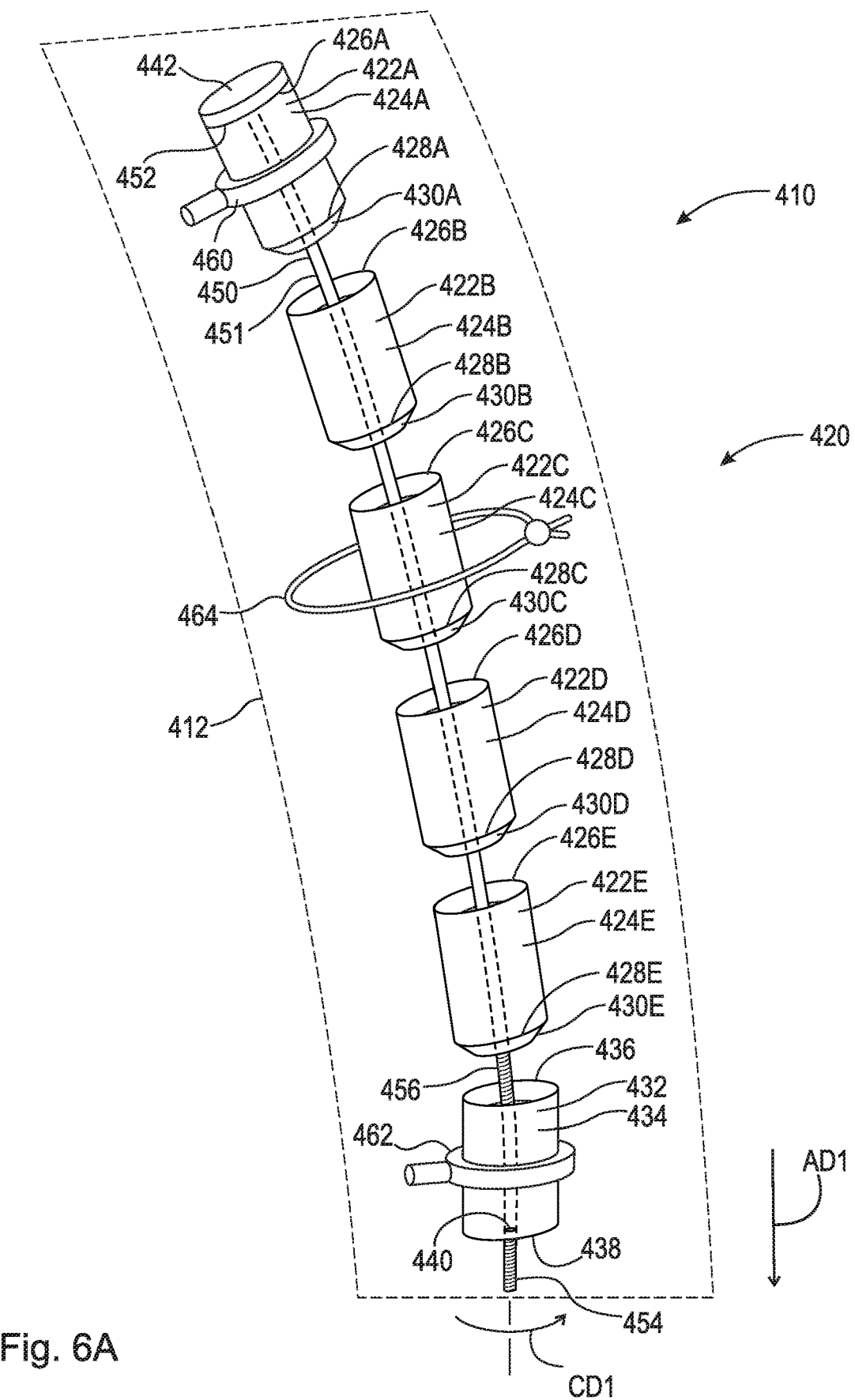
FIG. 6A is a perspective view of a segmented rod assembly.

FIG. 6A is a perspective view of segmented rod assembly 410. Segmented rod assembly 410 comprises rod 420, tensioning member 450, and winding assembly 200. Segmented rod assembly 410 may be enclosed or at least partially enclosed in flexible sheath 412. Flexible sheath 412 comprises a biocompatible material (e.g., polyethylene) to prevent tissue ingress or growth between rod segments.

Rod 420 comprises a plurality of segments arranged adjacent each other along tensioning member 450. In the embodiment shown, rod 420 is generally a hollow rod comprising segments 422A-E and 432. Segments 422A-E are substantially similar, but may differ in length. Preferably, each of segments 422A-E comprises a length which is similar to that of the height of a vertebra. In an example embodiment, the segments proximate an extreme curvature of a pathologic spine may comprise a smaller height than the segments proximate a straighter spine curvature. This arrangement allows for a more gradual and efficient straightening of the pathologic spine. Rod 420 may comprise plastic (e.g., polyethylene), titanium, chromium, cobalt, or any other suitable material.

Segment 422A comprises body 424A, end 426A, end 428A, and engaging member 430A. Engaging member 430A is connected to end 428A and tapers therefrom. Engaging member 430A is arranged to engage end 426B of segment 422B. Segment 422B comprises body 424B, end 426B, end 428B, and engaging member 430B. Engaging member 430B is connected to end 428B and tapers therefrom. Engaging member 430B is arranged to engage end 426C of segment 422C. Segment 422C comprises body 424C, end 426C, end 428C, and engaging member 430C. Engaging member 430C is connected to end 428C and tapers therefrom. Engaging member 430C is arranged to engage end 426D of segment 422D. Segment 422D comprises body 424D, end 426D, end 428D, and engaging member 430D. Engaging member 430D is connected to end 428D and tapers therefrom. Engaging member 430D is arranged to engage end 426E of segment 422E. Segment 422E comprises body 424E, end 426E, end 428E, and engaging member 430E. Engaging member 430E is connected to end 428E and tapers therefrom. Engaging member 430E is arranged to engage end 436 of segment 432. Segment 432 comprises body 434, end 436, and end 438. End 438 comprises threaded through-hole 440. It should be appreciated that rod 420 may have any number of segments suitable to be secured to and gradually straighten a pathologic spine. As is apparent to one having ordinary skill in the art, rod 420 must have enough segments to adequately canvas the subject curvature of the pathologic spine.

Tensioning member 450 is arranged inside of rod 420. Specifically, tensioning member 450 passes through segments 422A-E and 432. In the embodiment shown, tensioning member 450 is embodied as flexible shaft 451 having end 452 and end 454. Flexible shaft 451 further comprises threaded section 456 proximate end 454 which are arranged to engage threaded through-hole 440. Flexible shaft 451 is a device for transmitting rotary motion between two objects which are not fixed relative to one another. In the embodiment shown, end 452 is rotatably secured to plate 452. In an example embodiment, end 452 may also include a threaded portion which engages a threaded hole in plate 452. The threading of the threaded hole in plate 452 should be opposite of that of threaded through-hole 440 such that when flexible shaft 451 is rotated, segments 422A and 432 are pulled toward each other. This allows segmented rod assembly 410 to tauten even faster. Plate 442 is arranged to abut against or connect to end 426A. In an example embodiment, plate 442 is integrally formed with segment 422A and is fixed to end 426A. End 454 extends through segment 432 out of end 438, specifically through-hole 440. As flexible shaft 451 is turned, for example in circumferential direction CD1, threaded section 456 is forced out of threaded through-hole 440 in axial direction AD1. The arrangement of segments 422A-E and 432 on line 451 resembles that of beads on a string. As flexible shaft 451 is tautened, plate 442 pulls segments 422A-E and 432 together. As segments 422A-E and 432 begin to engage, rod 420 becomes increasingly rigid. Once segments 422A-E and 432 are fully engaged, rod 420 resembles a single rigid rod.

Segmented rod assembly 410 further comprises a plurality of anchors. As shown, segmented rod assembly 410 comprises anchors 460, 462, and 464 for connecting rod 420 to the pathologic spine. Anchor 460 is slidably connected to segment 422A and is secured to a cranial vertebra using, for example, a spinous process clamp, a pedicle screw, or other similar method of fixation. Anchor 460 is slidably connected to segment 422A such that as the pathologic spine straightens, and thereby lengthens, segmented rod assembly 410 adjusts to the length of the spine. To account for the increase in length, segment 422A may be significantly longer than the other segments. Anchor 462 is fixedly secured to segment 432 and is secured to a caudal vertebra using, for example, a spinous process clamp, a pedicle screw, or other similar method of fixation. Anchor 464 is slidably connected to segment 422C and is connected to the apex vertebra. Similar to anchor 460, anchor 464 is slidably connected to segment 422C to adjust for the straightening and lengthening of the spine. In an example embodiment, anchor 464 is fixedly connected to segment 422C. It should be appreciated that anchor 464 does not need to be slidably connected to segment 422C, but can be connected to any segment that is arranged near the apex vertebra such that the pathologic spine may be suitably straightened.

Figure 6B:
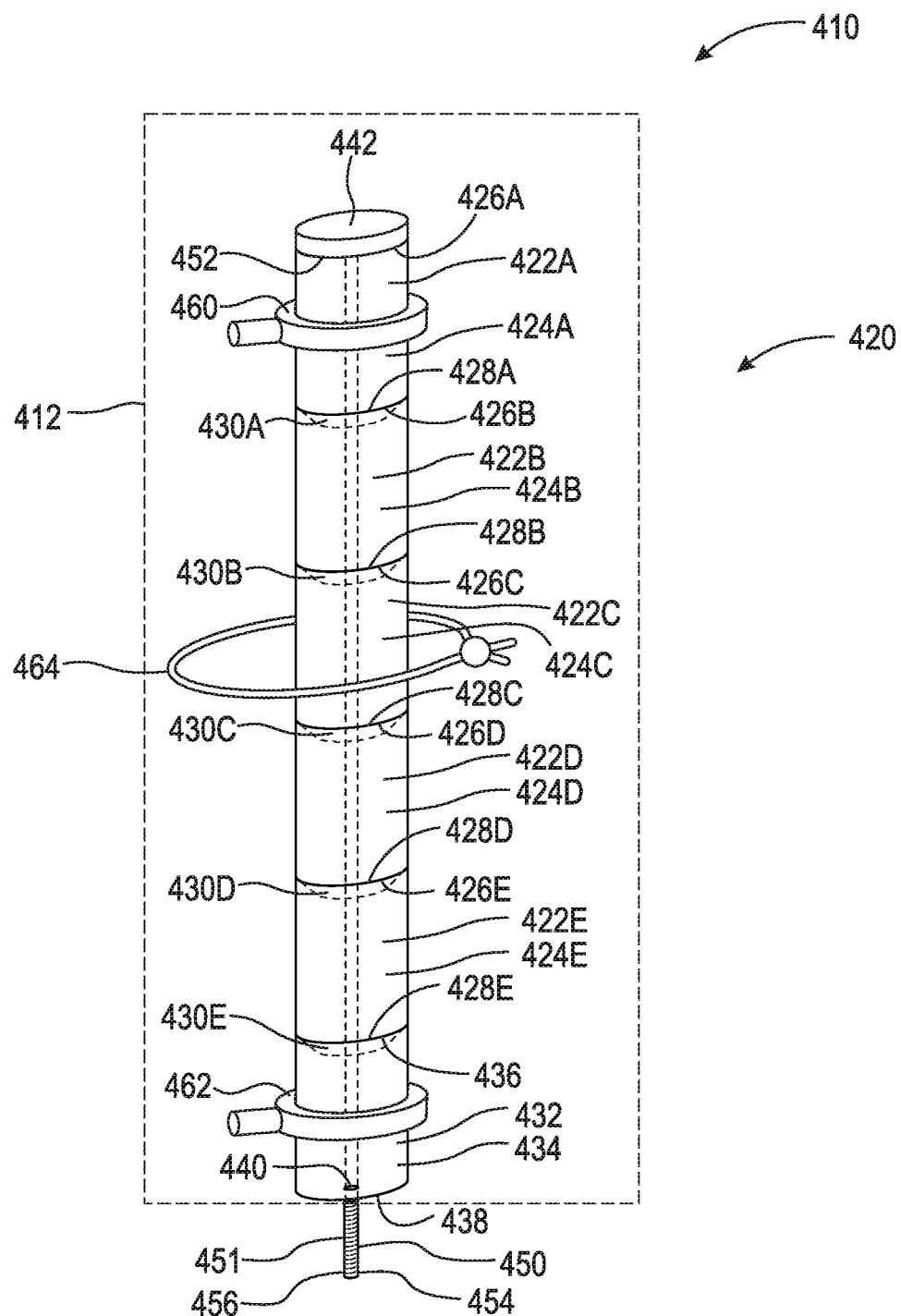
FIG. 6B is a perspective view of the segmented rod assembly shown in FIG. 6A, in a rigid rod alignment.

FIG. 6B is a perspective view of segmented rod assembly 410 in a rigid rod alignment. As shown, the segments of rod 420 are fully engaged with each other. Flexible shaft 451 is tautened such that plate 442 is pulled toward segment 432. Plate 442 abuts against end 426A of segment 422A. Engaging member 430A is fully engaged with segment 422B such that end 428A abuts against end 426B. Engaging member 430B is fully engaged with segment 422C such that end 428B abuts against end 426C. Engaging member 430C is fully engaged with segment 422D such that end 428C abuts against end 426D. Engaging member 430D is fully engaged with segment 422E such that end 428D abuts against end 426E. Engaging member 430E is fully engaged with segment 432 such that end 428E abuts against end 436. Flexible shaft 451 may be turned using any suitable means, for example, using modified winding assembly or gear system.

It should be appreciated that rod 420, when rigid, does not need to form a linear rod. The design of rod 420, when rigid, may imitate the normal curvature of the human spine (i.e., thoracic curvature, sacral curvature, lumbar curvature, cervical curvature, etc.). FIG. 6B demonstrates simply how the various segments engage in order form a rigid rod. The rod shown in FIG. 6B could be employed to correct lateral curvature of a pathologic spine.

FIG. 7A is a top perspective view of segment 22A of segmented rod assembly 10. FIG. 7B is a bottom elevational view of segment 22A. As shown, segment 22A comprises a generally square or rectangular cross-section. Segment 22A comprises body 24A, end 26A, end 28A, and engaging element 30A. Engaging element 30A is connected to end 28A and tapers therefrom.

FIG. 8A is a top perspective view of segment 322. Segment 322 is an example embodiment of a segment of segmented rod assembly 10. FIG. 8B is a bottom elevational view of segment 322. As shown, segment 322 comprises a generally circular cross-section. Segment 322 comprises body 324, end 326, end 328, and engaging element 330. Engaging element 330 is connected to end 328 and tapers therefrom.

FIG. 9A is a top perspective view of segment 422A of segmented rod assembly 410 (as shown in FIGS. 6A-B). Segment 422A is also an example embodiment of a segment of segmented rod assembly 10. FIG. 9B is a bottom elevational view of segment 422A. As shown, segment 422A comprises a generally ovular/oblong cross-section. Segment 422A comprises body 424A, end 426A, end 428A, and engaging element 430A. Engaging element 430A is connected to end 428A and tapers therefrom.

FIG. 10A is a top perspective view of segment 522. Segment 522 is an example embodiment of a segment of segmented rod assembly 10. FIG. 10B is a bottom elevational view of segment 522. As shown, segment 522 comprises a generally triangular cross-section. Segment 522 comprises body 524, end 526, end 528, and engaging element 530. Engaging element 530 is connected to end 528 and tapers therefrom.

Figure 11:
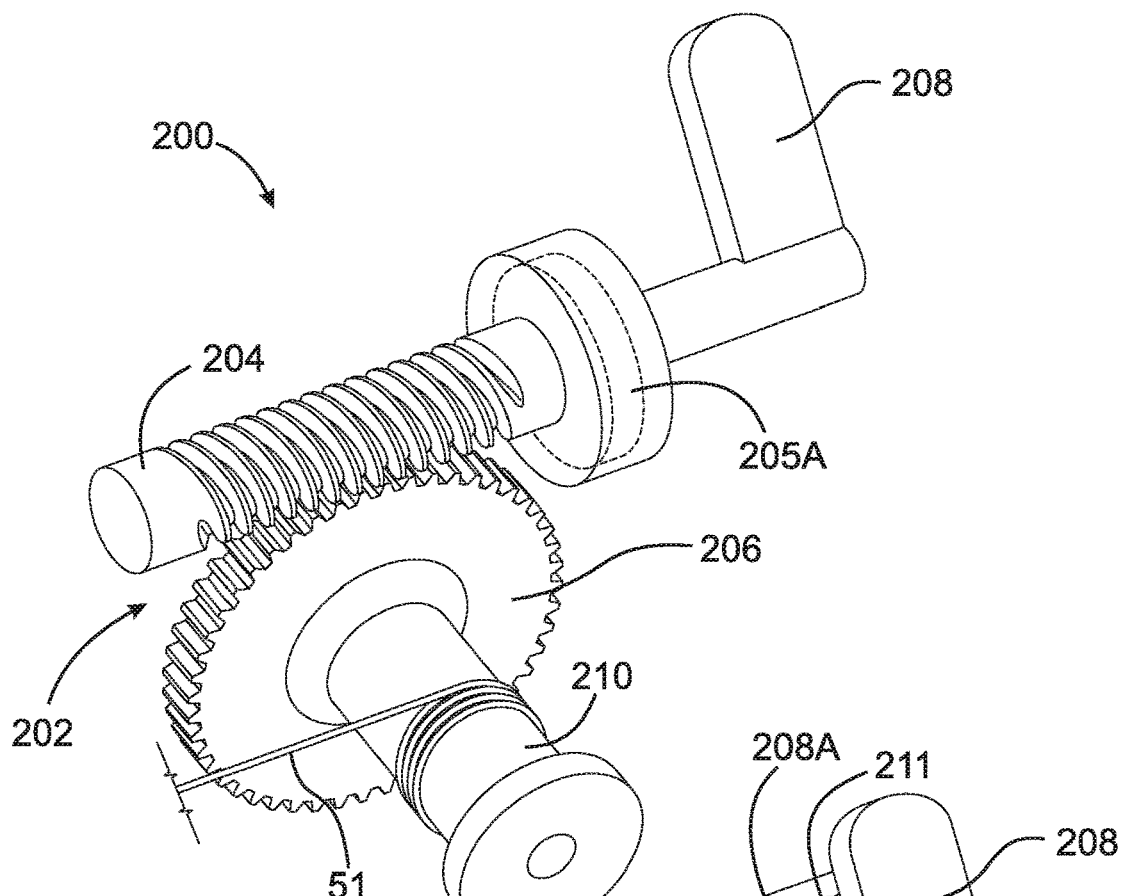
FIG. 11 is a top perspective view of a winding assembly for performing a gradual lateral spinal alignment of a spine.

FIG. 11 is a top perspective view of winding assembly 200 for performing a gradual lateral spinal alignment of a spine. In the configuration shown, the winding means is in the form of ratcheting mechanism 202, for example, a worm gear, which includes screw 204 that interacts with wheel 206. It should be appreciated that screw 204 could be a worm screw and that wheel 206 could be a worm wheel. Wheel 206 includes stem 210, which holds or retains line 51. Control lever 208 acts as a control means and is operatively attached to screw 204 to turn screw 204 a predetermined amount when pressed. By "operatively attached" it is meant that a component or device is connected either directly or indirectly to a second component and causes that second component to function, e.g., turn a predetermined amount. As can be seen in FIG. 11, when screw 204 turns, wheel 206 also rotates which in turn rotates stem 210 to wind line 51.

It should be appreciated that due to the frictional relationship between screw 204 and wheel 206, wheel 206 cannot rotate screw 204. Spring 205A is provided to enable control lever 208 to rebound to its starting position so that control lever 208 can only be moved a predetermined amount when pressed. Spring 205A is in the form of a torsion spring, for example. It should be appreciated that wheel 206, and thus stem 210, is activated by activating the actuator. In the embodiment shown in FIGS. 11 and 12, the actuator, control lever 208, is actuated by applying a physical force to control lever 208 through the skin (i.e., a doctor or medical professional can activate control lever 208 and tighten line 51). In an example embodiment, control lever 208 may be actuated by repetitive digital compression transcutaneously.

Figure 12:
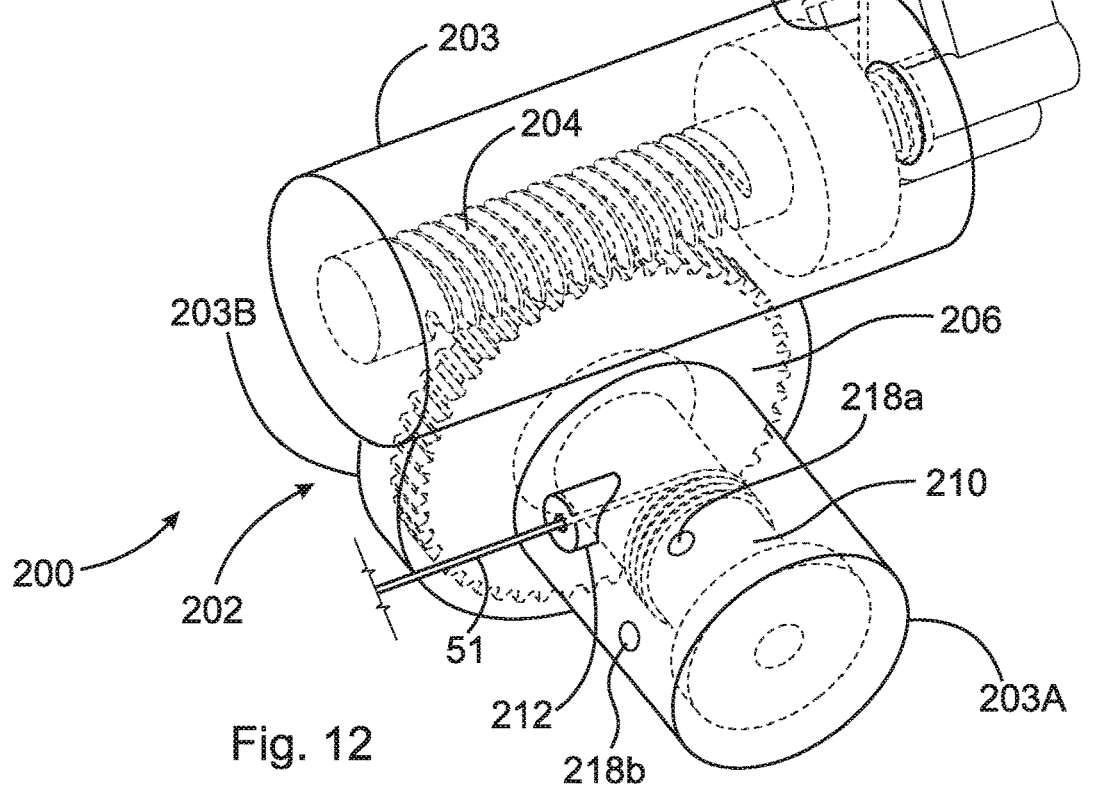
FIG. 12 is a top perspective view of the winding assembly shown in FIG. 11 enclosed in a housing.

FIG. 12 is a top perspective view of winding assembly 200 shown in FIG. 11 enclosed in a housing. FIG. 12 is a top perspective view of ratcheting mechanism 202 enclosed in housing 203. It is apparent to those having skill in the art that housing 203 may be a single unit enclosing ratcheting mechanism 202 or may include separately elements that enclose the individual components of ratcheting mechanism 202, such as housing 203A, enclosing stem 210 as seen in FIG. 12. It should be appreciated that housing 203 can be made of any suitable casing for example, a silicone elastomer. Preferably, spring 205B is included to enable control lever 208 to rebound to its starting position creating a ratchet effect so that control lever 208 can only be moved a predetermined amount when pressed. Spring 205B can be in the form of a coil spring attached to housing 203 in which control lever 208 is caused to return to a starting position. Control lever 208 may rebound to a starting position off coil spring 211 attached to rebound board 208A. Persons having ordinary skill in the art recognize that although FIGS. 11-12 depict different spring means that act to return control lever 208 to a starting position, preferably, only one spring means is utilized in any one particular ratcheting mechanism 202.

Figure 13:
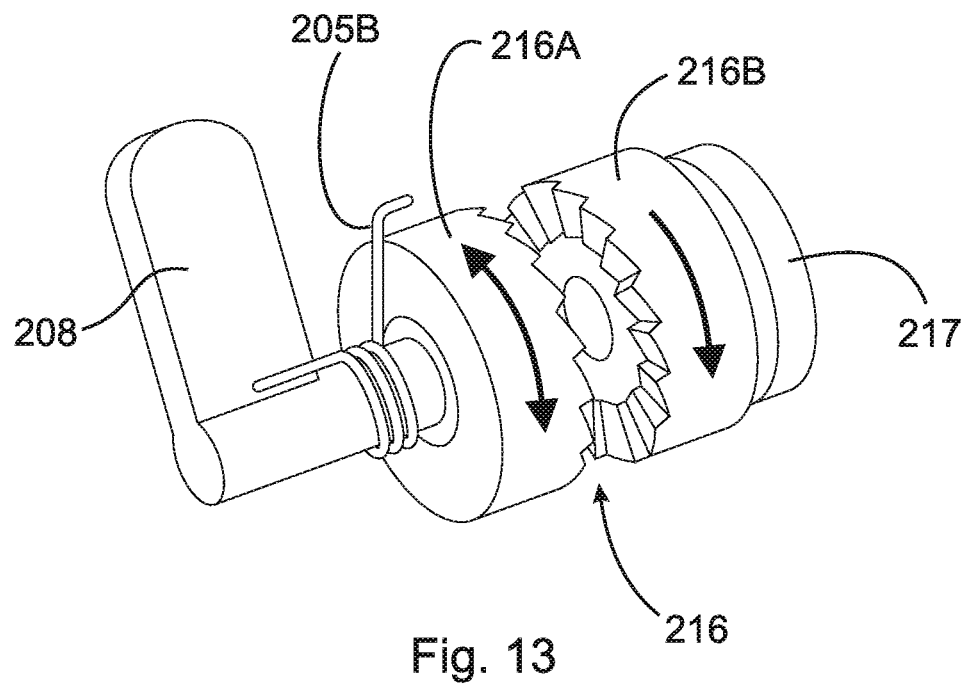
FIG. 13 is a top perspective view of a ratchet assembly used in an example embodiment of a winding assembly for performing gradual spinal alignments.
Figure 14:
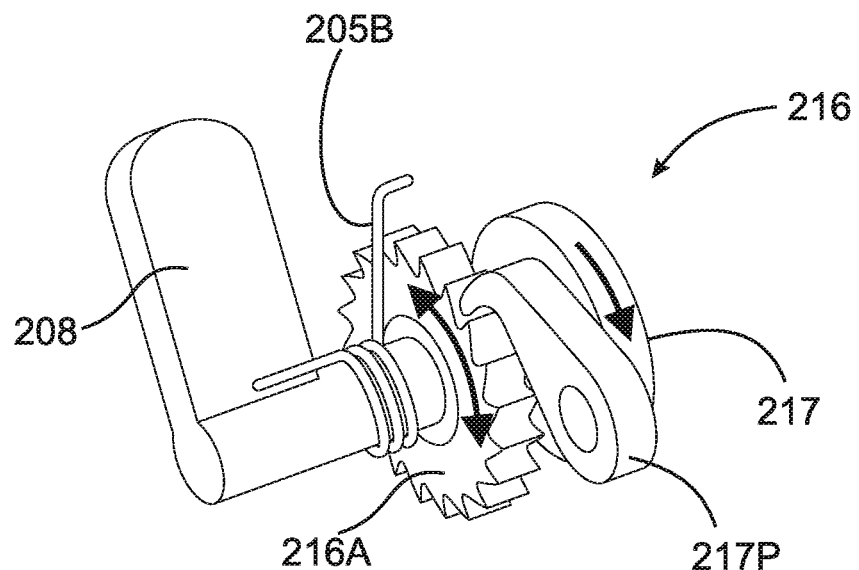
FIG. 14 is a top perspective view of a ratchet assembly used in an example embodiment of a winding assembly for performing gradual spinal alignments.

FIG. 13 is a top perspective view of ratchet assembly 216 used in an example embodiment of winding assembly 200 for performing gradual spinal alignments. FIG. 14 is a top perspective view of ratchet assembly 216 used in an example embodiment of winding assembly 200 for performing gradual spinal alignments. The winding means may be a ratchet mechanism used to control the rotation of stem 210 through ratcheting mechanism 202, or directly through control of ratchet assembly 216 as shown in FIGS. 13 and 14. In FIG. 13, control lever 208 is operatively attached to ratchet gear 216A, which engages ratchet gear 216B to rotate ratchet gear 216B in a single direction. In FIG. 14, control lever 208 is operatively attached to a single ratchet gear 216A and control lever 208 can rotate ratchet gear 216A in a single direction via pawl 217P. Pawl 217P is connected to housing 203 surrounding ratchet assembly 216 (shown in FIG. 12). Spring 217 acts to maintain rotational tension in ratchet assembly 216 to return control lever 208 to its starting position. Persons having ordinary skill in the art recognize that a worm screw, such as screw 204, may be attached to ratchet assembly 216 to enable ratcheting mechanism 202 to be rotated a predetermined amount and thus pull line 51 a predetermined amount with each press of control lever 208.

Figure 15:
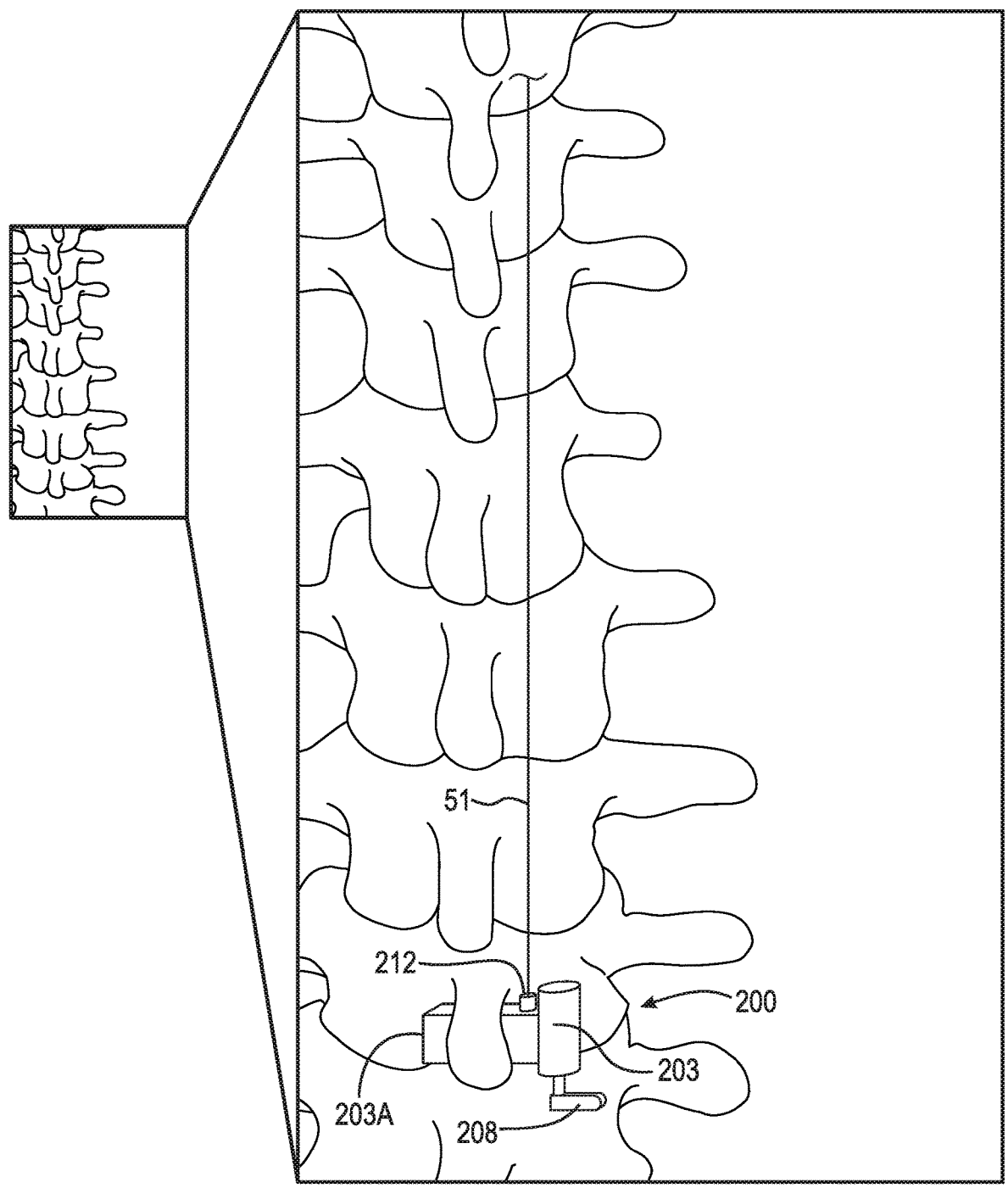
FIG. 15 is a perspective view of the winding assembly shown in FIG. 11 secured to a vertebra of a spinal column with screws.

FIG. 15 is a perspective view of winding assembly 200 shown in FIG. 12, secured to a vertebra of a spinal column with screws 220a and 220b. Specifically, winding assembly 200 is secured to a spinous process of a vertebra. Winding assembly 200 is secured to the spinous process of a vertebra proximate the caudal segment of segmented rod assembly 10 (i.e., a vertebra proximate segment 32). In an example embodiment, winding assembly 200 is secured to the spinous process of a vertebra proximate the cranial segment of segmented rod assembly 10 (i.e., a vertebra proximate segment 22A). In an example embodiment, winding assembly 200 is secured to the caudal segment of segmented rod assembly 10 (i.e., end 38 of segment 32). In an example embodiment, winding assembly 200 is secured to the cranial segment of segmented rod assembly 10 (i.e., end 26A of segment 22A). The components of ratcheting mechanism 202 are enclosed in housings 203, 203A, and 203B. FIG. 15 also includes a posterior schematic view of a spinal column comprising vertebrae and intervertebral disks. In an example embodiment, ratcheting mechanism 202 is secured to one of the vertebrae via one or more screws. The one or more screws pass through respective one or more through-bores of housing 203A, respectively, and secure into the vertebra. Preferably, ratcheting mechanism 202 is attached in such a way as to allow control lever 208 to be proximate to the external side of surrounding tissue to enable it to be operated, e.g., pressed, from outside the body of a patient. Although not shown in FIG. 15, preferably, a spring means such as those discussed above, is included in winding assembly 200 to ensure line 51 is wound only a predetermined amount when control lever 208 is pressed, once identified by palpation through the skin. In this exemplary embodiment, control lever 208 can be activated subcutaneously to create force on line 51.

In an example embodiment, winding assembly 200 comprises an actuator portion that can be actuated to create tension in line 51. For example, winding assembly 200 can include an actuator portion having a magnetic motor that allows tension to be put on line 51 by use of an External Remote Controller. In another example, winding assembly 200 includes an actuator or a motor that can be energized with radio frequency or ultrasonic energy. It should be appreciated that any suitable means of continuously creating tension in line 51 may be used.

Figure 16:
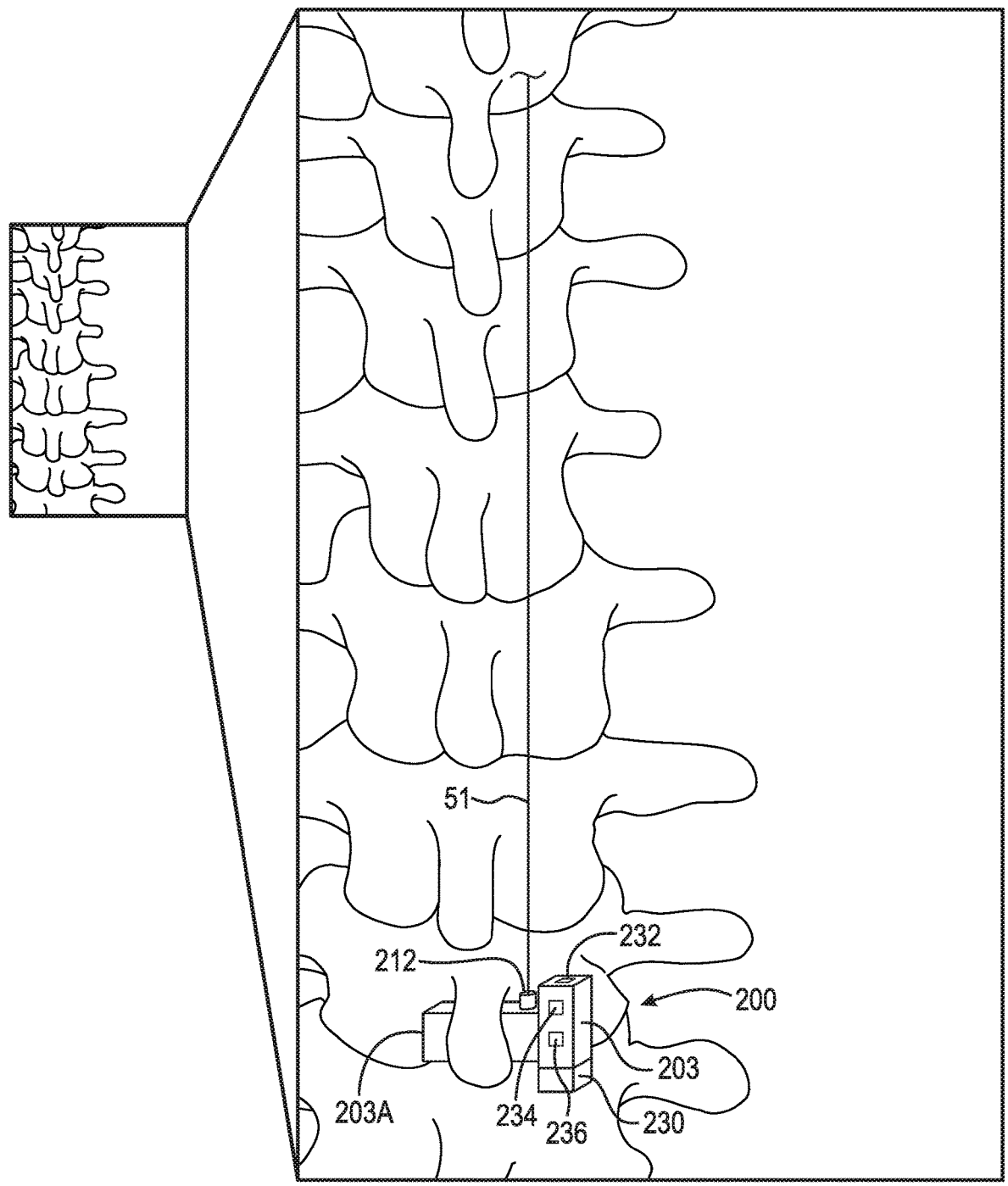
FIG. 16 is an example embodiment showing a motor as an actuator portion.

FIG. 16 is an example embodiment showing motor 230 as an actuator portion that creates tension in line 51. In this example embodiment, motor 230 that drives wheel 206, and thus stem 210. Motor 230 includes wireless receiver 232 that, when a signal is sent to receiver 232, activates motor 230. In this example embodiment, motor 230 can be actuated by wireless communications such as radio frequency transmission (i.e., radio waves), optical wireless communication (i.e., light), ultrasound communication (i.e., sending signals using ultrasonic waves), other electromagnetic wireless technologies, such as magnetic or electric fields, or any other suitable signal known to those of ordinary skill in the art. In this example embodiment, motor 230 may be an ultrasonic motor, a piezoelectric motor, or an ultrasonic piezoelectric motor, as is known to those of ordinary skill in the art. Receiver 232 may be an ultrasound transducer, specifically a receiver or transceiver, capable of converting ultrasound into electric signals. Motor 230 may also include power source 234. Power source 234 may be, for example, a battery. In an example embodiment, motor 230 may be powered externally by radio frequency or ultrasound energy, as is known in the art. Piezoelectric motors are favored for their high power to weight ratio, high torque, reliability and lack of need for maintenance, controllability to a nanometer level, silence, lack of need for a gear box, and, more recently, improved cost. Piezoelectric motors are increasingly being used in robotics and could easily be used to power winding assembly 200, and create tension in line 51, with or without a worm drive gearing mechanism. In an example embodiment, multiple short rods are implanted at different locations along the spine at a curvature, each with its own anchor and cable and operated by a micro motor. Motor 230 may also include programmable computer 236. Programmable computer is implanted with motor 230 such that the rate of tensioning in line 51 could be preprogrammed days or weeks at a time.

Figure 17A:
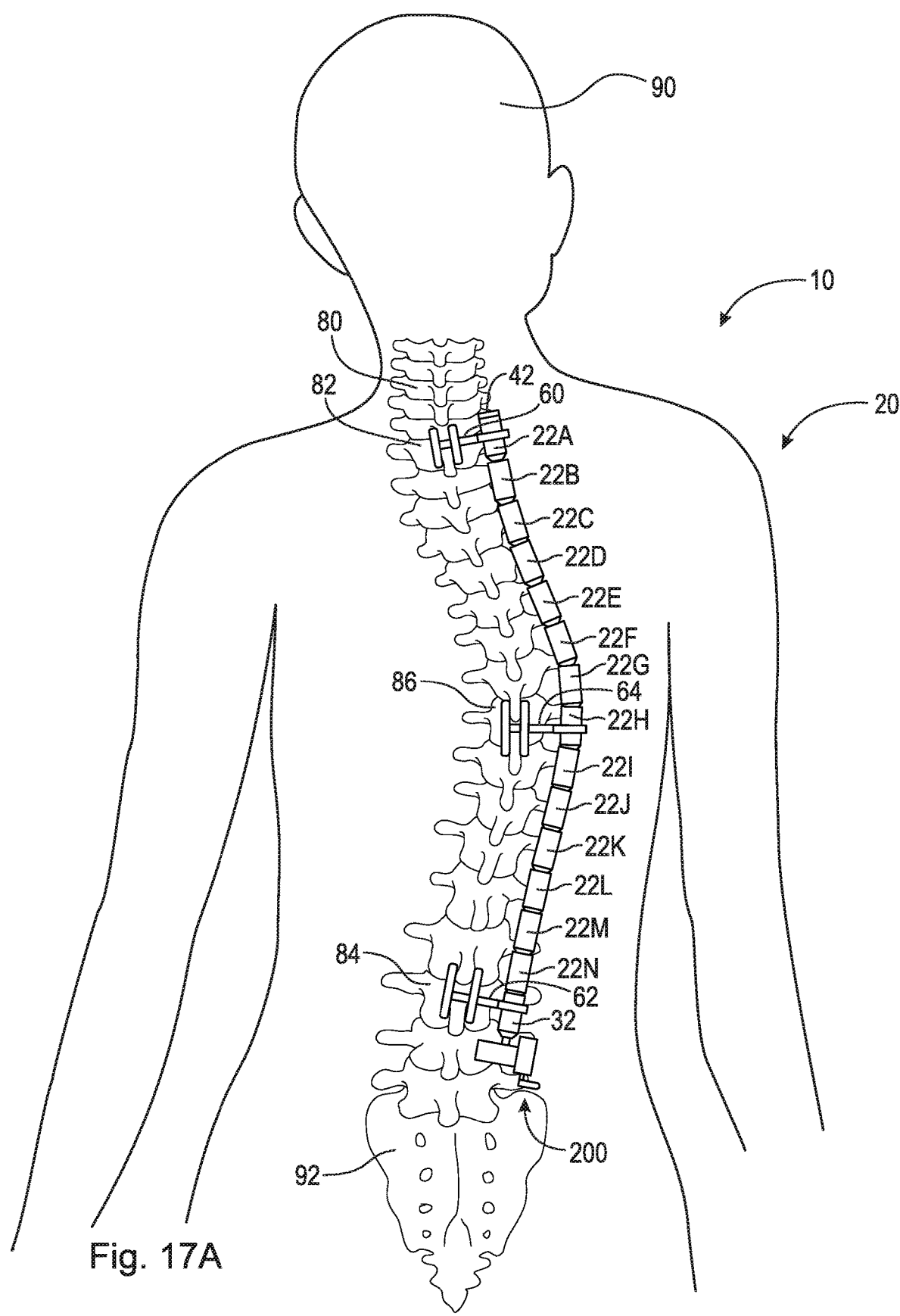
FIG. 17A is an elevational view of a segmented rod assembly connected to a pathologic spine.

FIG. 17A is an elevational view of segmented rod assembly 10 connected to (pathologic) spine 80. In the embodiment shown, rod 20 comprises segments 22A-N and 32. Segment 22A is slidably secured to cranial vertebra 82 via anchor 60. Cranial vertebra 82 is a vertebra of spine 80 generally located proximate cranium 90. Cranial vertebra 82 may also be the end vertebra of the curve on the cranial side. As is known in the art, the end vertebra of a curve is that with the maximal tilt toward the apex of the curve. Anchor 60 may be secured to the spinous process of cranial vertebra 82 using, for example, a spinous process clamp, pedicle screw, or any other suitable securing means. Segment 32 is fixedly secured to caudal vertebra 84 via anchor 62. Caudal vertebra 84 is a vertebra of spine 80 generally located proximate coccyx 92. Caudal vertebra 82 may also be the end vertebra of the curve on the caudal side. As is known in the art, the end vertebra of a curve is that with the maximal tilt toward the apex of the curve. Anchor 62 may be secured to the spinous process of caudal vertebra 84 using, for example, a spinous process clamp, pedicle screw, or any other suitable securing means. Segment 2211 is connected to apex vertebra 86 via anchor 64. Apex vertebra 86 is a vertebra of spine 80 with the greatest rotation or farthest deviation from the center of the vertebral column. Anchor 64 may be secured to the spinous process of apex vertebra 86 using, for example, a spinous process clamp, pedicle screw, or any other suitable securing means. As shown, line 51 has not yet been tautened, leaving segments 22B-N to float relative to spine 80. Segment 22A may slide relative to spine 80. Segment 32 and winding assembly 200 is fixedly secured to caudal vertebra 84 and therefore cannot move relative to spine 80. Segment 2211 may be fixedly secured or slidingly connected to apex vertebra 86. Plate 42 is shown unconnected to segment 22A; however, in an example embodiment, plate 42 is fixedly secured to segment 22A. It should be appreciated that segmented rod assembly 10 may be arranged on the opposite side of spine 80 (i.e., the left side). Segmented rod assembly 10 is shown offset from the vertebrae of spine 80. However, it should be appreciated that segmented rod assembly 10 can be arranged along the spino-laminar junction. It should also be appreciated that two segmented rod assemblies may be used on either side of the spinous process of spine 80 for added force.

Figure 17B:
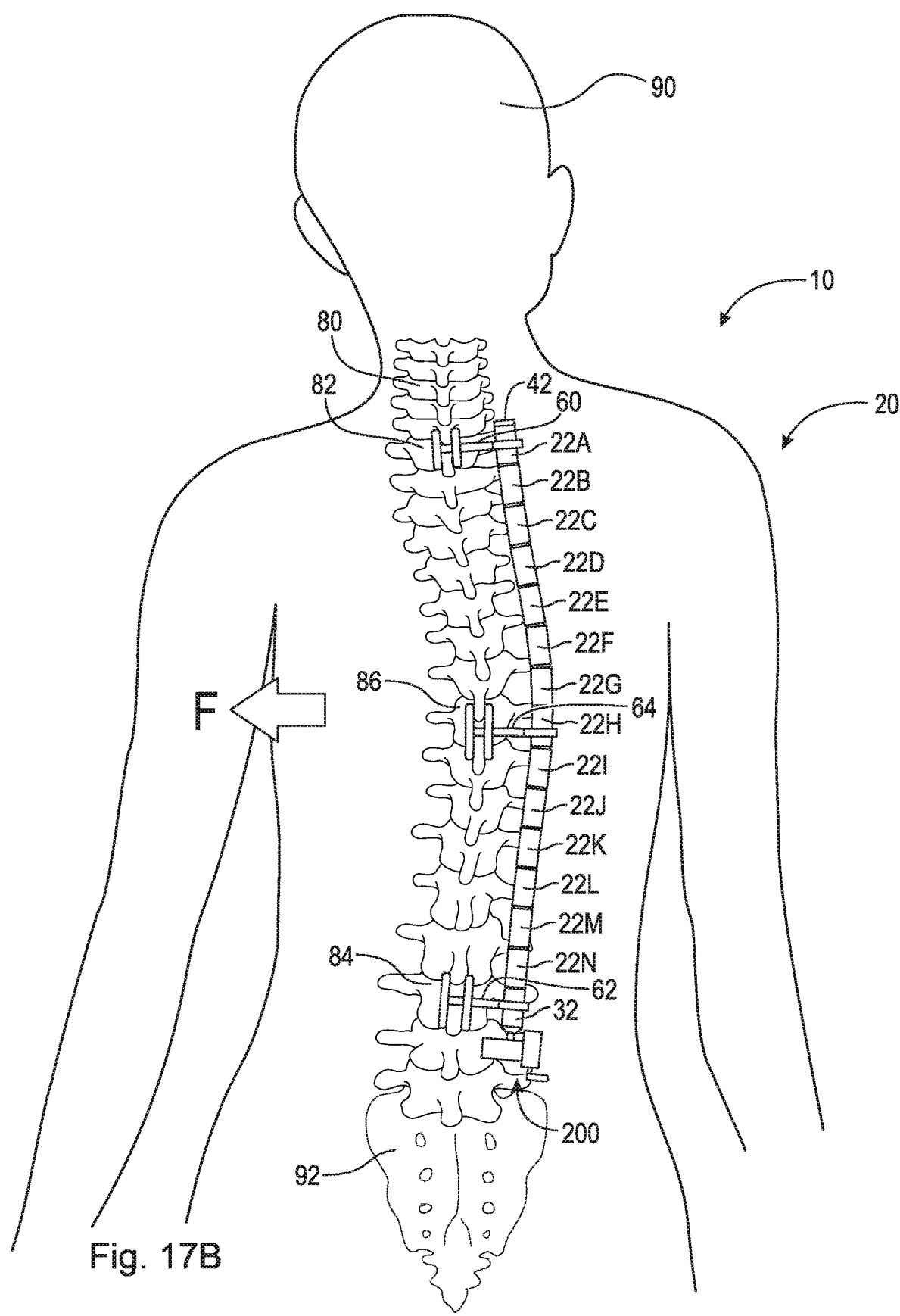
FIG. 17B is an elevational view of the segmented rod assembly connected to the pathologic spine shown in FIG. 17A, with the segmented rod assembly partially engaged.

FIG. 17B is an elevational view of segmented rod assembly 10 connected to (pathologic) spine 80. As shown, line 51 has been tautened via winding assembly 200 and segmented rod assembly 10 partially engaged. Segments 22A-N and 32 of rod 20 are at least partially engaged with each other. Some of segments 22A-N and 32 may be fully engaged with each other. Line 51 should be taut, which results in straightening forces being asserted on (pathologic) spine 80. The straightening forces in the embodiment shown are designed by arrow F. Over time, these straightening forces will cause apex vertebra 86, and adjacent vertebrae, back into alignment with the rest of the vertebral column and thereby straighten spine 80. In the embodiment shown, segmented rod assembly 10 "pushes" apex vertebra 86 toward alignment with cranial vertebra 82 and caudal vertebra 84. However, segmented rod assembly 10 could be arranged on the opposite side of spine 80 (left side), and "pull" apex vertebra 86 toward alignment with cranial vertebra 82 and caudal vertebra 84.

Figure 17C:
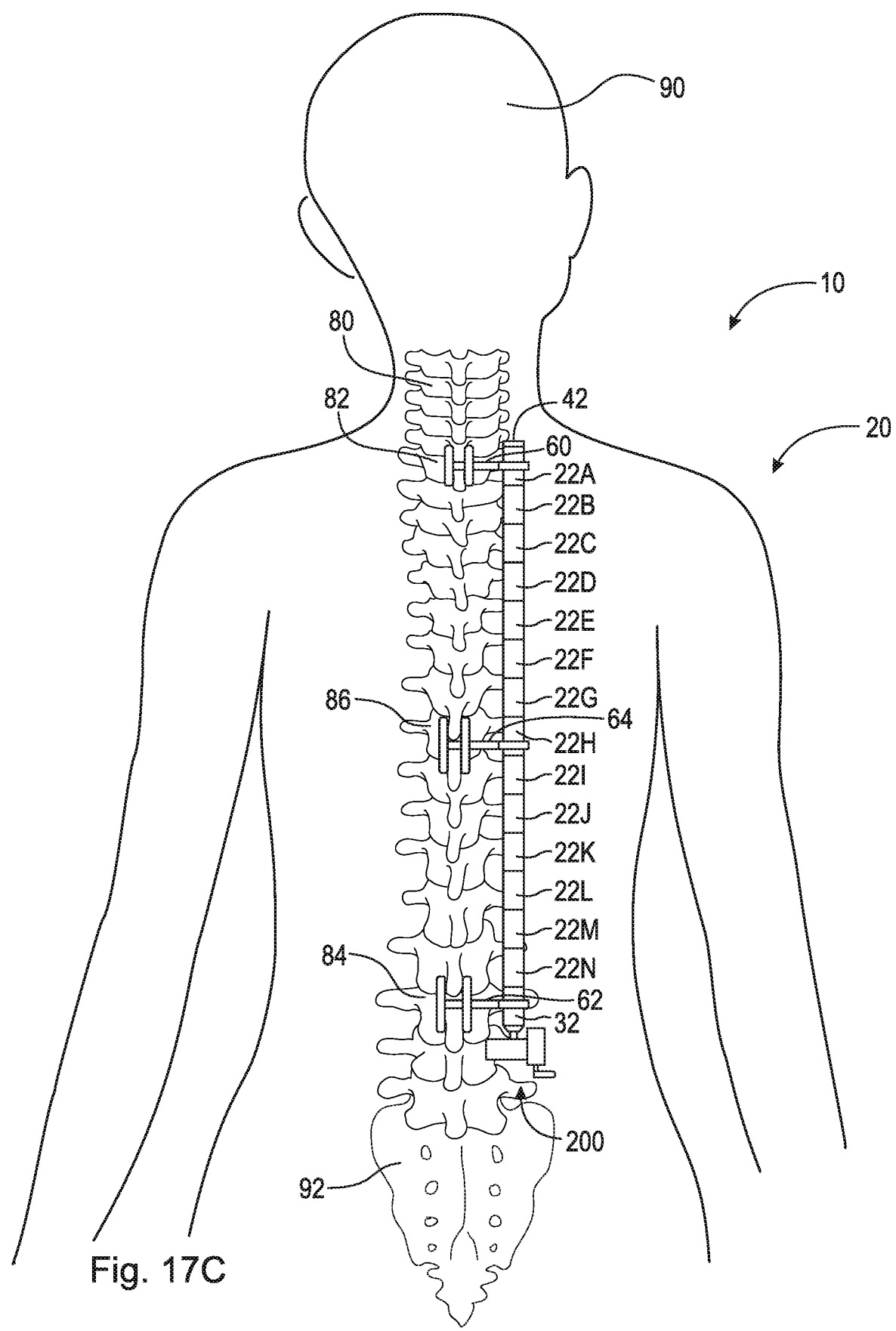
FIG. 17C is an elevational view of the segmented rod assembly connected to the pathologic spine shown in FIG. 17A, with the segmented rod assembly fully engaged.

FIG. 17C is an elevational view of segmented rod assembly 10 connected to spine 80. As shown, line 51 has been further tautened via winding assembly 200 and segmented rod assembly 10 fully engaged. Segments 22A-N and 32 of rod 20 are fully engaged with each other, which allows rod 20 to take its final rigid shape. It should be appreciated that, although rigid rod 20 is shown to be linear, rigid rod 20 can be designed with three-dimensional curvature to best suit the patient. As shown, apex vertebra 86 has been aligned with cranial vertebra 82 and caudal vertebra 84 to form a straightened spine 80.

Figure 18:
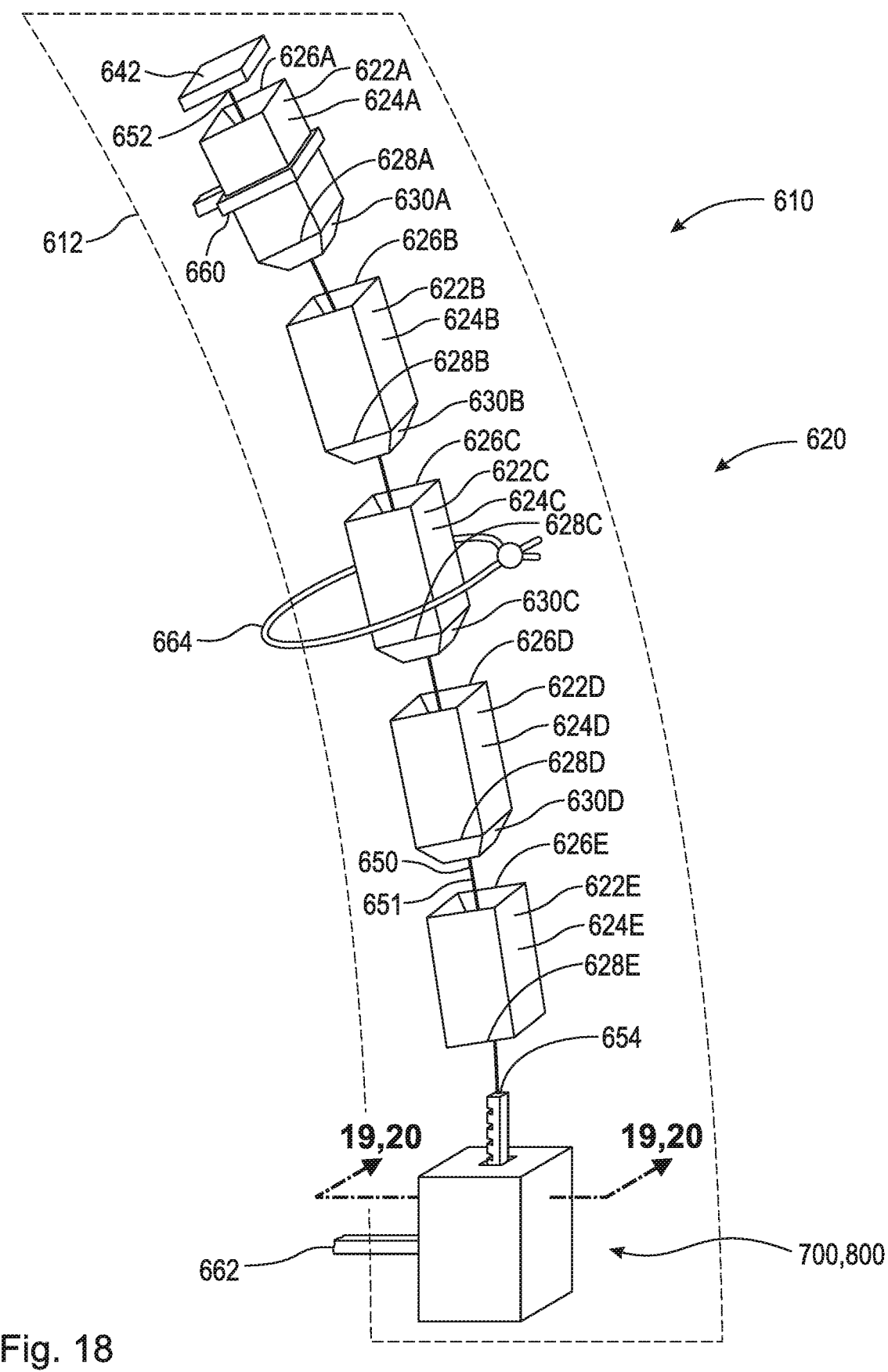
FIG. 18 is a perspective view of a segmented rod assembly.

FIG. 18 is a perspective view of segmented rod assembly 610. Segmented rod assembly 610 comprises rod 620, tensioning member 650, and winding assembly 700 or 800. Segmented rod assembly 610 may be enclosed or at least partially enclosed in flexible sheath 612. Flexible sheath 612 comprises a biocompatible material (e.g., polyethylene) to prevent tissue ingress or growth between rod segments.

Rod 620 comprises a plurality of segments arranged adjacent each other along tensioning member 650. In the embodiment shown, rod 620 is generally a hollow rod comprising segments 622A-E. Segments 22A-E are substantially similar, but may differ in length. Preferably, each of segments 622A-E comprises a length which is similar to that of the height of a vertebra. In an example embodiment, the segments proximate an extreme curvature of a pathologic spine may comprise a smaller height than the segments proximate a straighter spine curvature. This arrangement allows for a more gradual and efficient straightening of the pathologic spine. Rod 620 may comprise plastic (e.g., polyethylene), titanium, chromium, cobalt, or any other suitable material.

Segment 622A comprises body 624A, end 626A, end 628A, and engaging member 630A. Engaging member 630A is connected to end 628A and tapers therefrom. Engaging member 630A is arranged to engage end 626B of segment 622B. Segment 622B comprises body 624B, end 626B, end 628B, and engaging member 630B. Engaging member 630B is connected to end 628B and tapers therefrom. Engaging member 630B is arranged to engage end 626C of segment 622C. Segment 622C comprises body 624C, end 626C, end 628C, and engaging member 630C. Engaging member 630C is connected to end 628C and tapers therefrom. Engaging member 630C is arranged to engage end 626D of segment 622D. Segment 622D comprises body 624D, end 626D, end 628D, and engaging member 630D. Engaging member 630D is connected to end 628D and tapers therefrom. Engaging member 630D is arranged to engage end 626E of segment 622E. Segment 622E comprises body 624E, end 626E, and end 628E. End 628E is arranged to engage winding assembly 600 and 700. As shown, end 628E is arranged to abut against and/or secure to winding assembly 600 and 700. It should be appreciated that rod 620 may have any number of segments suitable to be secured to and gradually straighten a pathologic spine. As is apparent to one having ordinary skill in the art, rod 620 must have enough segments to adequately canvas the subject curvature of the pathologic spine.

Tensioning member 650 is arranged inside of rod 620. Specifically, tensioning member 650 passes through segments 22A-E. In the embodiment shown, tensioning member 650 is embodied as line 651 having end 652 and end 654. Line 651 may be a cable, plurality of cables, string, rope, chain, or any other flexible material suitable to draw segments 622A-E together upon tautening. End 652 is connected to plate 642. Plate 642 is arranged to abut against or connect to end 626A. In an example embodiment, plate 642 is integrally formed with segment 622A and is fixed to end 626A. End 654 extends through segment 622E out of end 628E and is connected to winding assembly 600 or 700. The arrangement of segments 622A-E on line 651 resembles that of beads on a string. As line 651 is tautened via winding assembly 600 and 700, plate 642 pulls segments 622A-E together. As segments 622A-E begin to engage, rod 620 becomes increasingly rigid. Once segments 622A-E are fully engaged, rod 620 resembles a single rigid rod.

Segmented rod assembly 610 further comprises a plurality of anchors. As shown, segmented rod assembly 610 comprises anchors 660, 662, and 664 for connecting rod 620 to the pathologic spine. Anchor 660 is slidably connected to segment 622A and is secured to a cranial vertebra using, for example, a spinous process clamp, a pedicle screw, or other similar method of fixation. Anchor 660 is slidably connected to segment 622A such that as the pathologic spine straightens, and thereby lengthens, segmented rod assembly 610 adjusts to the length of the spine. To account for the increase in length, segment 622A may be significantly longer than the other segments. Anchor 662 is fixedly secured to winding assembly 700 or 800 and is secured to a caudal vertebra using, for example, a spinous process clamp, a pedicle screw, or other similar method of fixation. Specifically, anchor 662 fixedly secures housing 702 to at least one caudal vertebra (see FIG. 19) or anchor 662 fixedly secures housing 802 to at least one caudal vertebra (see FIG. 20). Anchor 664 is slidably connected to segment 622C and is connected to the apex vertebra. Similar to anchor 660, anchor 664 is slidably connected to segment 622C to adjust for the straightening and lengthening of the spine. In an example embodiment, anchor 664 is fixedly connected to segment 622C. It should be appreciated that anchor 664 does not need to be slidably connected to segment 622C, but can be connected to any segment that is arranged near the apex vertebra such that the pathologic spine may be suitably straightened.

Figure 19:
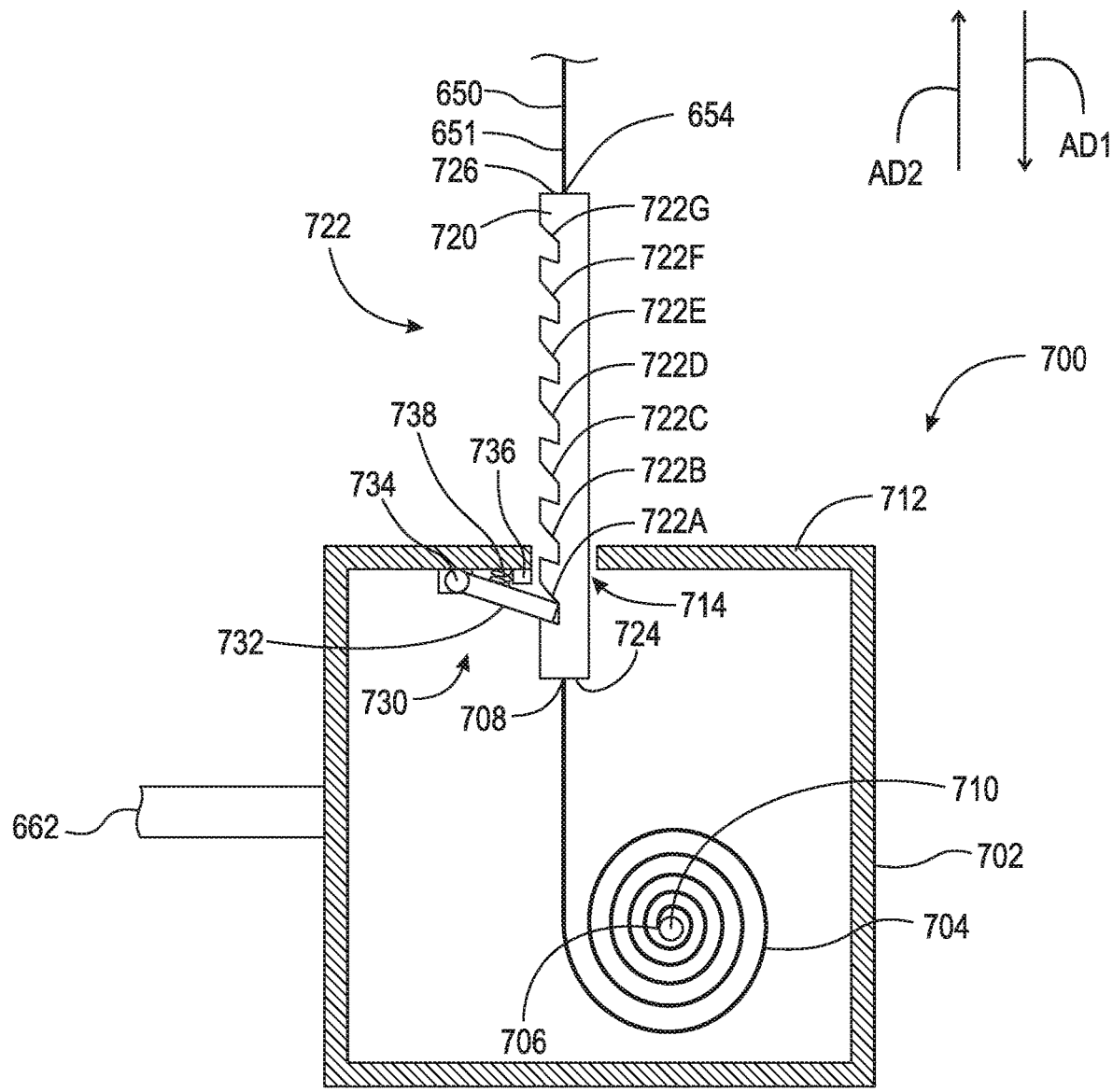
FIG. 19 is a cross-sectional view of the ratcheting spring assembly taken generally along line 19-19 in FIG. 18; and, FIG. 20 is a cross-sectional view of the ratcheting spring assembly taken generally along line 20-20 in FIG. 18.

FIG. 19 is a cross-sectional view of winding assembly 700 taken generally along line 19-19 in FIG. 18. Winding assembly 700 generally comprises housing 702, spring 704, bar 720, and ratchet assembly 730. Housing 702 is arranged to be fixedly secured to at least one vertebra, as previously described. Bar 720 comprises notches 722, end 724, and end 726. End 654 of line 651 is connected to end 726. Bar 720 extends into housing 702 through hole 714 in plate 712. In the embodiment shown, bar 720 comprises notches 722A-G. However, it should be appreciated that bar 720 may have any number of notches, having any geometric shape, suitable for engaging with ratchet assembly 730 to form a ratchet. Spring 704 is a constant force spring connected to bar 720 and housing 702. Specifically, spring 704 comprises end 706, which is connected to housing 702 via anchor 710, and end 708, which is connected to end 724 of bar 720. Spring 704 is preloaded such that bar 720 is biased in axial direction AD1. It should be appreciated that spring 704 may comprise any suitable spring to provide continuous force on bar 720, and that the instant invention should not be limited to only constant force springs. Bar 720 is arranged to engage ratchet assembly 730. Ratchet assembly 730 comprises pawl 732, which is hingedly connected to plate 712 via hinge 734, and fulcrum 736, which is connected to plate 712 proximate hole 714. Ratchet assembly 730 further comprises spring 738 connected to pawl 738 and plate 712. In an example embodiment, spring 738 is connected to pawl 738 and fulcrum 736. Spring 738 is arranged to bias pawl 732 in a counterclockwise direction such that pawl 732 abuts against fulcrum 736. Pawl 732 is arranged to engage notches 722. As shown, pawl 732 is engaged with notch 722A. As line 651 loosens, bar 720 is displaced in axial direction AD1 via tension in spring 704. The arrangement of ratchet assembly 730 allows bar to displace in axial direction AD1 but not in axial direction AD2. Specifically, hinge 734 allows pawl 732 to rotate clockwise but fulcrum 736 prevents pawl from rotating counter clockwise. As bar 720 displaces in axial direction AD1, pawl 732 displaces in a clockwise direction thereby disengaging from, for example, notch 722A. Once bar 720 displaces a sufficient amount, with spring 738 biasing pawl 732 in a counter clockwise direction, pawl 732 engages, for example, notch 722B. This process will continue until all of segments 622A-E are fully engaged with each other and the spine is straight. It should be appreciated that rod 620, when rigid, does not need to form a linear rod. It should be appreciated that when pawl 732 is fully engaged with one of notches 722, bar 720 and thus tensioning member 650 are prevented from displacing in axial direction AD2. When pawl 732 is not fully engaged with one of notches 722, bar 720 and thus tensioning member 650 may be displaceable in axial direction AD2 a nominal distance, as is apparent to one having ordinary skill in the art. The design of rod 620, when rigid, imitates the normal curvature of the human spine (i.e., thoracic curvature, sacral curvature, lumbar curvature, cervical curvature, lateral curvature, etc.). It should also be appreciated that any suitable ratcheting assembly may be used, and that one having ordinary skill in the art can envision various other ratcheting assemblies suitable for allowing bar 720 to move in axial direction AD1 but limit or prevent bar from moving in axial direction AD2.

Figure 20:
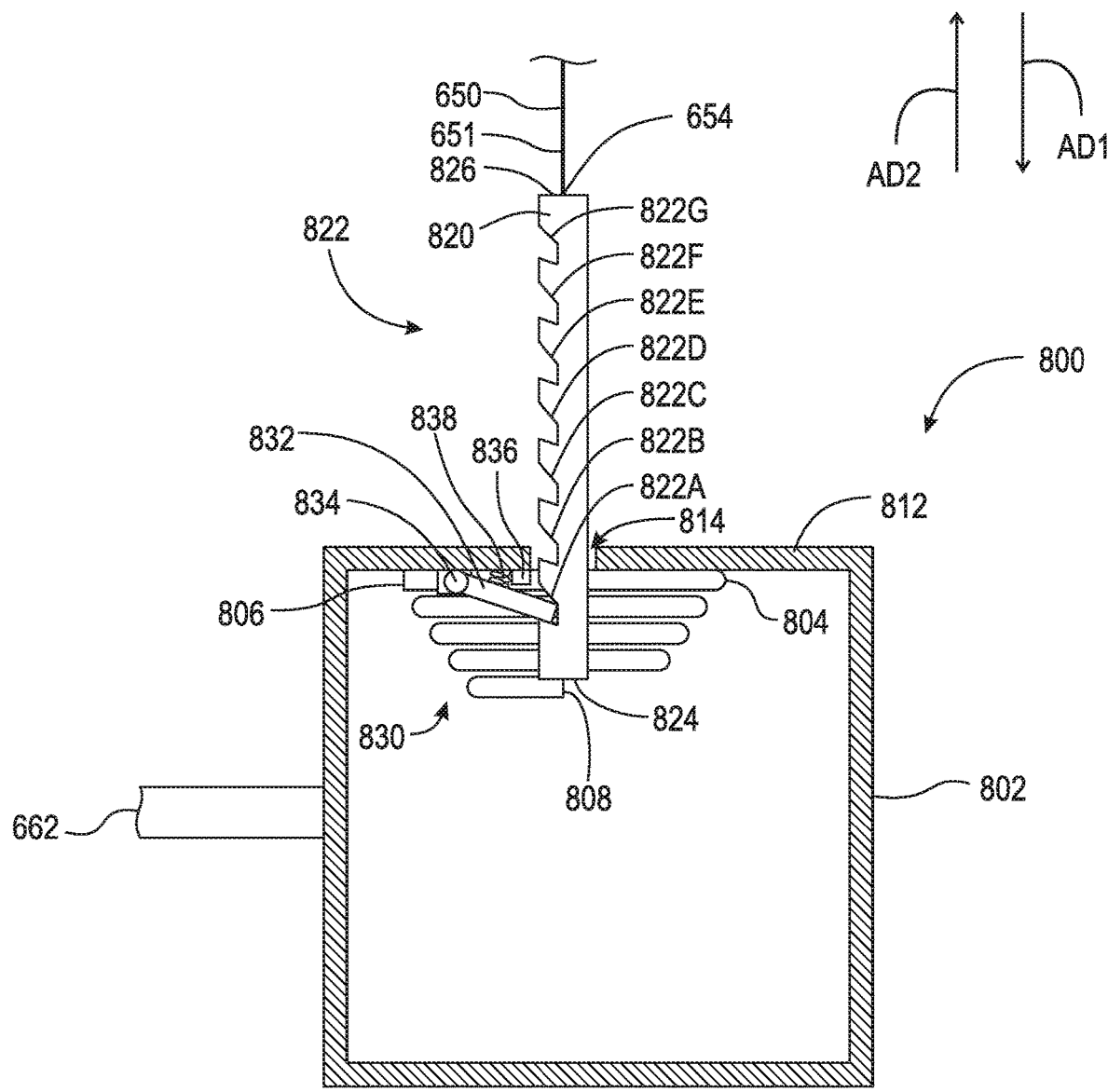

FIG. 20 is a cross-sectional view of winding assembly 800 taken generally along line 20-20 in FIG. 18. Winding assembly 800 generally comprises housing 802, spring 804, bar 820, and ratchet assembly 830. Housing 802 is arranged to be fixedly secured to at least one vertebra, as previously described. Bar 820 comprises notches 822, end 824, and end 826. End 654 of line 651 is connected to end 826. Bar 820 extends into housing 802 through hole 814 in plate 812. In the embodiment shown, bar 820 comprises notches 822A-G. However, it should be appreciated that bar 820 may have any number of notches, having any geometric shape, suitable for engaging with ratchet assembly 830 to form a ratchet. Spring 804 is a conical or frustoconical spring connected to bar 820 and housing 802. Specifically, spring 804 comprises end 806, which is connected to and/or abuts against housing 802, and end 808, which is connected to end 824 of bar 820. Spring 804 is preloaded such that bar 820 is biased in axial direction AD1. It should be appreciated that spring 804 may comprise any suitable spring to provide continuous force on bar 820, for example a coil or helical spring, and that the instant invention should not be limited to only conical and frustoconical springs. Bar 820 is arranged to engage ratchet assembly 830. Ratchet assembly 830 comprises pawl 832, which is hingedly connected to plate 812 via hinge 834, and fulcrum 836, which is connected to plate 812 proximate hole 814. Ratchet assembly 830 further comprises spring 838 connected to pawl 838 and plate 812. In an example embodiment, spring 838 is connected to pawl 838 and fulcrum 836. Spring 838 is arranged to bias pawl 832 in a counterclockwise direction such that pawl 832 abuts against fulcrum 836. Pawl 832 is arranged to engage notches 822. As shown, pawl 832 is engaged with notch 822A. As line 651 loosens, bar 820 is displaced in axial direction AD1 via tension in spring 804. The arrangement of ratchet assembly 830 allows bar to displace in axial direction AD1 but not in axial direction AD2. Specifically, hinge 834 allows pawl 832 to rotate clockwise but fulcrum 836 prevents pawl from rotating counter clockwise. As bar 820 displaces in axial direction AD1, pawl 832 displaces in a clockwise direction thereby disengaging from, for example, notch 822A. Once bar 820 displaces a sufficient amount, with spring 838 biasing pawl 832 in a counter clockwise direction, pawl 832 engages, for example, notch 822B. This process will continue until all of segments 622A-E are fully engaged with each other and the spine is straight. It should be appreciated that rod 620, when rigid, does not need to form a linear rod. It should be appreciated that when pawl 832 is fully engaged with one of notches 822, bar 820 and thus tensioning member 650 are prevented from displacing in axial direction AD2. When pawl 832 is not fully engaged with one of notches 822, bar 820 and thus tensioning member 650 may be displaceable in axial direction AD2 a nominal distance, as is apparent to one having ordinary skill in the art. The design of rod 620, when rigid, imitates the normal curvature of the human spine (i.e., thoracic curvature, sacral curvature, lumbar curvature, cervical curvature, lateral curvature, etc.). It should also be appreciated that any suitable ratcheting assembly may be used, and that one having ordinary skill in the art can envision various other ratcheting assemblies suitable for allowing bar 820 to move in axial direction AD1 but limit or prevent bar from moving in axial direction AD2.

It should be appreciated that the various segments of this disclosure may be hollow or may be solid having a throughbore through which the line or rod extends.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

P Person
1 Spinal column
2 Upper curve
3 Lower curve
4 Brace
5 Brace
10 Segmented rod assembly
20 Rod
22A Segment
24A Body
26A End
28A End
30A Engaging element
22B Segment
24B Body
26B End
28B End
30B Engaging element
22C Segment
24C Body
26C End
28C End
30C Engaging element
22D Segment
24D Body
26D End
28D End
30D Engaging element
22E Segment
24E Body
26E End
28E End
30E Engaging element
32 Segment
34 Body
36 End
38 End
42 Plate
50 Tensioning member
51 Line
52 End
54 End
60 Anchor
62 Anchor
64 Anchor
80 Spine
82 Cranial vertebra
84 Caudal vertebra
86 Apex vertebra
90 Cranium
92 Coccyx
110 Segmented rod assembly
120 Rod assembly
122A Segment
124A Body
126A End
128A End
130A Partition
122B Segment
124B Body
126B End
128B End
130B Partition
122C Segment
124C Body
126C End
128C End
130C Partition
122D Segment
124D Body
126D End
128D End
130D Partition
122E Segment
124E Body
126E End
128E End
130E Partition
132 Segment
134 Body
136 End
138 End
140 Partition
142 Plate
150 Tensioning member
151 Line
152 End
154 End
160 Anchor
162 Anchor
170A Hinge
170B Hinge
170C Hinge 170D Hinge
170E Hinge
200 Winding assembly
202 Ratcheting mechanism
203 Housing
203A Housing
203B Housing
204 Screw
205A Spring
205B Spring
206 Wheel
208 Control lever
208A Rebound board
210 Stem
211 Coil spring
212 Port
216 Ratchet assembly
216A Ratchet gear
216B Ratchet gear
217 Spring
217P Pawl
230 Motor
232 Receiver
234 Power source
236 Programmable computer
322 Segment
324 Body
326 End
328 End
330 Engaging element
410 Segmented rod assembly
420 Rod
422A Segment
424A Body
426A End
428A End
430A Engaging element
422B Segment
424B Body
426B End
428B End
430B Engaging element
422C Segment
424C Body
426C End
428C End
420C Engaging element
422D Segment
424D Body
426D End
428D End
430D Engaging element
422E Segment
424E Body
426E End
428E End
430E Engaging element
432 Segment
434 Body
436 End
438 End
440 Threaded through-hole
442 Plate
450 Tensioning member
451 Flexible shaft
452 End
454 End
456 Threaded section
60 Anchor
62 Anchor
64 Anchor
522 Segment
524 Body
526 End
528 End
530 Engaging element
610 Segmented rod assembly
620 Rod
622A Segment
624A Body
626A End
628A End
630A Engaging element
622B Segment
624B Body
626B End
628B End
630B Engaging element
622C Segment
624C Body
626C End
628C End
630C Engaging element
622D Segment
624D Body
626D End
628D End
630D Engaging element
622E Segment
624E Body
626E End
628E End
642 Plate
650 Tensioning member
651 Line
652 End
654 End
660 Anchor
662 Anchor
664 Anchor
700 Winding assembly
702 Housing
704 Spring
706 End
708 End
710 Anchor
712 Plate
714 Hole
720 Bar
722 Notches
722A Notch
722B Notch
722C Notch
722D Notch
722E Notch
722F Notch
722G Notch
724 End
726 End
730 Ratchet assembly
732 Pawl
734 Hinge
736 Fulcrum
738 Spring 800 Winding assembly
802 Housing
804 Spring
806 End
808 End
812 Plate
814 Hole
820 Bar
822 Notches
822A Notch
822B Notch
822C Notch
822D Notch
822E Notch
822F Notch
822G Notch
824 End
826 End
830 Ratchet assembly
832 Pawl
834 Hinge
836 Fulcrum
838 Spring
AD1 Axial direction
AD2 Axial direction
CD1 Circumferential direction
F Force

What is claimed is:

1. A segmented rod assembly for aligning a spine having a plurality of vertebrae, comprising:
   a rod, including:
      a plurality of segments, the plurality of segments having at least:
         a first segment arranged to be slidingly secured to a first vertebra of the spine;
         a second segment arranged to be fixedly secured to a second vertebra of the spine; and,
         a third segment arranged between the first and second segments to be connected to a third vertebra of the spine;
      a tensioning member arranged within the plurality of segments, the tensioning member having a first end secured to the first segment and a second end; and,
      a winding mechanism, including:
         a bar including a third end connected to the second end, a fourth end, and one or more notches arranged along a length of the bar from the third end to the fourth end; and,
         a spring connected to the fourth end and arranged to bias the tensioning member in a first axial direction.

2. The segmented rod assembly as recited in claim 1, wherein the tensioning member is a line.

3. The segmented rod assembly as recited in claim 1, wherein the winding mechanism is arranged proximate the second segment and is operatively arranged to displace the tensioning member relative to the second segment in the first axial direction to pull the first and third segments toward the second segment.

4. The segmented rod assembly as recited in claim 1, wherein when the first segment and the second segment, or the second segment and the third segment, are connected, they do not rotate with respect to each other.

5. The segmented rod assembly as recited in claim 3, wherein each of the plurality of segments are operatively arranged to engage with an adjacent segment.

6. The segmented rod assembly as recited in claim 5, wherein at least one of the plurality of segments comprises:
   a body including a top end and a bottom end; and,
   an engaging member connected to the bottom end and tapering therefrom.

7. The segmented rod assembly as recited in claim 3, wherein each of the plurality of segments are hingedly connected with an adjacent segment.

8. The segmented rod assembly as recited in claim 1, wherein the tensioning member is a flexible shaft.

9. The segmented rod assembly as recited in claim 8, wherein the first end is rotatably connected to the first segment and the second end is threadably connected to the second segment.

10. The segmented rod assembly as recited in claim 1, wherein the rod comprises a material selected from: polyethylene, titanium, chromium, or cobalt.

11. The segmented rod assembly as recited in claim 1, wherein:
    in a fully engaged state, the plurality of segments are rigidly connected with each other; and,
    in a partially engaged or relaxed state, the plurality of segments are at least partially spaced with each other.

12. The segmented rod assembly as recited in claim 1, further comprising a sheath arranged to encase the rod.

13. The segmented rod assembly as recited in claim 1, wherein the winding mechanism further comprises
    a ratchet assembly operatively arranged to engage the one or more notches, wherein when the ratchet assembly is engaged with one of the one or more notches it prevents displacement of the tensioning member in a second axial direction, opposite the first axial direction.

14. The segmented rod assembly as recited in claim 13, wherein the ratchet assembly comprises a pawl pivotably connected to a housing of the winding mechanism, the pawl operatively arranged to engage the one or more notches.

15. The segmented rod assembly as recited in claim 7, wherein each of the plurality of segments are operatively arranged to abut against an adjacent segment.

16. The segmented rod assembly as recited in claim 1, wherein the spring comprises a constant force spring comprising:
    a proximal end connected to the second end; and,
    a distal end anchored to a housing of the winding mechanism.

17. The segmented rod assembly as recited in claim 1, wherein the spring is at least partially conical.

18. The segmented rod assembly as recited in claim 1, wherein the first, second, and third segments each have a non-circular cross-section.

19. The segmented rod assembly as recited in claim 1, wherein the spring applies a linear force to the bar in the first axial direction.

20. The segmented rod assembly as recited in claim 14, wherein the ratchet assembly further comprises a pawl spring operatively arranged to bias the pawl in the second axial direction.

21. A segmented rod assembly for aligning a spine having a plurality of vertebrae, comprising:
    a rod, including:
       a plurality of segments, the plurality of segments having at least:
          a first segment arranged to be slidingly secured to a first vertebra of the spine;
          a second segment arranged to be fixedly secured to a second vertebra of the spine; and,
          a third segment arranged between the first and second segments to be connected to a third vertebra of the spine, wherein each of the plurality of segments are hingedly connected with an adjacent segment; and,
a tensioning member arranged within the plurality of segments, the tensioning member having a first end secured to the first segment and a second end.

22. A segmented rod assembly for aligning a spine having a plurality of vertebrae, comprising:
a rod, including:
a plurality of segments, the plurality of segments having at least:
a first segment arranged to be slidingly secured to a first vertebra of the spine;
a second segment arranged to be fixedly secured to a second vertebra of the spine; and,
a third segment arranged between the first and second segments to be connected to a third vertebra of the spine;
a tensioning member arranged within the plurality of segments, the tensioning member having a first end secured to the first segment and a second end; and,
a spring connected to the second end and operatively arranged to apply a linear force to the tensioning member in a first axial direction.

* * * * *